US010040831B2

(12) United States Patent
Bond et al.

(10) Patent No.: US 10,040,831 B2
(45) Date of Patent: Aug. 7, 2018

(54) COMPOSITIONS AND METHODS FOR TREATING DISEASES BY INHIBITING EXOSOME RELEASE

(71) Applicant: MOREHOUSE SCHOOL OF MEDICINE, Atlanta, GA (US)

(72) Inventors: Vincent C. Bond, Stone Mountain, GA (US); James W. Lillard, Jr., Smyrna, GA (US); Ming Bo Huang, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 15/383,454

(22) Filed: Dec. 19, 2016

(65) Prior Publication Data

US 2018/0170969 A1    Jun. 21, 2018

(51) Int. Cl.

| A61K 38/16 | (2006.01) |
| A61K 47/64 | (2017.01) |
| C07K 14/00 | (2006.01) |
| C07K 19/00 | (2006.01) |
| C07K 14/005 | (2006.01) |
| A61K 47/48 | (2006.01) |
| A61K 45/06 | (2006.01) |
| C12N 7/00 | (2006.01) |

(52) U.S. Cl.
CPC .......... *C07K 14/005* (2013.01); *A61K 38/162* (2013.01); *A61K 45/06* (2013.01); *A61K 47/48215* (2013.01); *A61K 47/64* (2017.08); *C12N 7/00* (2013.01); *C07K 2319/035* (2013.01); *C07K 2319/70* (2013.01); *C12N 2740/16022* (2013.01)

(58) Field of Classification Search
CPC ........ A61K 38/03; A61K 38/08; A61K 38/10; A61K 38/16; A61K 38/162; A61K 47/64; C07K 4/00; C07K 4/02; C07K 7/06; C07K 7/08; C07K 14/00; C07K 14/63; C07K 2319/01; C07K 2319/035; C07K 2319/70; C07K 2319/74
See application file for complete search history.

(56) References Cited

U.S. PATENT DOCUMENTS

| 4,569,789 A | 2/1986 | Blattler et al. |
| 4,631,190 A | 12/1986 | Shen et al. |
| 5,252,714 A | 10/1993 | Harris et al. |
| 5,306,809 A | 4/1994 | Boon et al. |
| 5,560,234 A | 10/1996 | Ross et al. |
| 5,569,754 A | 10/1996 | Williams et al. |
| 5,665,358 A | 9/1997 | Barton et al. |
| 5,672,662 A | 9/1997 | Harris et al. |
| 5,985,263 A | 11/1999 | Lee et al. |
| 5,990,237 A | 11/1999 | Bentley et al. |
| 2004/0192627 A1 | 9/2004 | Weissig et al. |
| 2012/0121507 A1 | 5/2012 | Filfil et al. |
| 2012/0171115 A1 | 7/2012 | Hudson et al. |
| 2013/0089525 A1 | 4/2013 | Bond et al. |
| 2014/0121170 A2 | 5/2014 | Bond et al. |
| 2014/0142121 A1 | 5/2014 | Altieri et al. |
| 2014/0196172 A1 | 7/2014 | Eudes et al. |
| 2016/0237129 A1 | 8/2016 | Keefe et al. |

FOREIGN PATENT DOCUMENTS

WO    99/03499    1/1999

OTHER PUBLICATIONS

International Search Report and Written Opinion of International Patent Application No. PCT/US2016/067616, dated Mar. 16, 2017.
Lee, M. C.S. et al., "Bi-directional protein transport between the ER and Golgi", Annu. Rev. Cell Dev. Biol., 2004, vol. 20, pp. 87-123.
Lippincott-Schwartz, J. et al., "Rapid redistribution of Golgi proteins into the ER in cells treated with brefeldin A: evidence for membrane cycling from Golgi to ER", Cell, 1989, vol. 56(5), pp. 801-813.
Misumi, Y. et al., "Novel blockade by brefeldin A of intracellular transport of secretory proteins in cultured rat hepatocytes", The Journal of Biological Chemistry, 1986, vol. 261(24), pp. 11398-11403.
Muesch, A. et al., "A Novel Pathway for Secretory Proteins?", Trends Biochem. Sci., 1990, vol. 15 (3), pp. 86-88.
Johnstone, R. M. et al., "Vesicle formation during reticulocyte maturation. Association of plasma membrane activities with released vesicles (exosomes)", The Journal of Biological Chemistry, 1987, vol. 262(19), pp. 9412-9420.
Nickel, W., "Unconventional secretory routes: direct protein export across the plasma membrane of mammalian cells", Traffic, 2005, vol. 6(8), pp. 607-614.
Guy, B. et al., "Mutational analysis of the HIV nef Protein", Virology, 1990, vol. 176, pp. 413-425.
Campbell, T. D. et al., "HIV-1 Nef protein is secreted into vesicles that can fuse with target cells and virions", Ethnicity & Disease, 2008, vol. 18(2), pp. S2-14-S2-19.
Sanfridson, A. et al., "Nef proteins encoded by human and simian immunodeficiency viruses induce the accumulation of endosomes and lysosomes in human T cells", Proc. Natl. Acad. Sci., 1997, vol. 94(3), pp. 873-838.
Esser, M. T. et al., "Differential Incorporation of CD45, CD80 (B7-1), CD86 (B7-2), and Major Histocompatibility Complex Class I and II Molecules into Human Immunodeficiency Virus Type 1 Virions and Microvesicles: Implications for Viral Pathogenesis and Immune Regulation", Journal of Virology, 2001, vol. 75(13), pp. 6173-6182.
Lindner, K. et al., "Circulating microRNAs: emerging biomarkers for diagnosis and prognosis in patients with gastrointestinal cancers", Clinical Science (Lond), 2015, vol. 128(1), pp. 1-15.

(Continued)

*Primary Examiner* — Jeffrey E. Russel
(74) *Attorney, Agent, or Firm* — Ping Wang; Morris, Manning & Martin, LLP

(57) ABSTRACT

A multipartite peptide that inhibits release of exosomes in a cell, comprising an N-terminal end and a C-terminal end and comprising at least one secretion modifying region (SMR) peptide from HIV-1 Nef and at least one Clusterin (Clu)-binding peptide (Clu-BP). Pharmaceutical compositions comprising these peptides alone or in synergistic combinations with other active agents in methods for treating cancers and/or infectious diseases are further provided herein.

13 Claims, 8 Drawing Sheets

(56) References Cited

OTHER PUBLICATIONS

Salido-Guadarram, I. et al., "MicroRNAs transported by exosomes in body fluids as mediators of intercellular communication in cancer", OncoTargets and Therapy, 2014, vol. 7, pp. 1327-1338.
Morris, M. C. et al., "A peptide carrier for the delivery of biologically active proteins into mammalian cells: Application to the Delivery of antibodies and therapeutic Proteins", Cell Biology, 2006, pp. 13-18.
Joliot, A. et al., "Transduction peptides: from technology to physiology", Nature Cell Biology, 2004, vol. 6(3), pp. 189-196.
Heitz, F. et al., "Twenty years of cell-penetrating peptides: from molecular mechanisms to therapeutics", British Journal of Pharmacology, 2009, vol. 157(2), pp. 195-206.
Gaertner, H. F. et al., "Site-specific attachment of functionalized poly(ethylene glycol) to the amino terminus of proteins", Bioconjugate Chem., 1996, vol. 7(1), pp. 38-44.
Stockert, J. C. et al., "MTT assay for cell viability: Intracellular localization of the formazan product is in lipid droplets", Acta Histochemica, 2012, vol. 114(8), pp. 785-796.
Riss, T. L. et al., "Cell Viability Assays", Assay Guidance Manual, 2013, pp. 1-31.
Ali, S. A. et al., "Genetic Characterization of HV Type 1 Nef-Induced Vesicle Secretion", AIDS Research and Human Retroviruses, 2010, vol. 26(2), pp. 173-192.
Ellman, G. L. et al., "A new and rapid colorimetric determination of acetylcholinesterase activity", Biochemical Pharmacology, 1961, vol. 7, pp. 88-95.
Shelton, M. N. et al., "Secretion Modification Region-Derived Peptide Disrupts HIV-1 Nef's Interaction with Mortalin and Blocks Virus and Nef Exosome Release", Journal of Virology, 2012, vol. 86(1), pp. 406-419.

SEQUENCE LISTING

<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Val Gly Phe Pro Val
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

```
<400> SEQUENCE: 2

Val Gly Phe Pro Val Ala Ala Val Gly Phe Pro Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

His Pro Leu Ser Lys His Pro Tyr Trp Ser Gln Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Asn Thr Tyr Trp Ser Gln Leu Leu His Phe Gln Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Ser His Ala Leu Pro Leu Thr Trp Ser Thr Ala Ala
1               5                   10

<210> SEQ ID NO 6
<211> LENGTH: 24
<212> TYPE: PRT
<213> ORGANISM: Artificial Sequence
<220> FEATURE:
<223> OTHER INFORMATION: Synthetic

<400> SEQUENCE: 6

Val Gly Phe Pro Val Ala Ala Val Gly Phe Pro Val His Pro Leu Ser
1               5                   10                  15

Lys His Pro Tyr Trp Ser Gln Pro
            20

<210> SEQ ID NO 7
<211> LENGTH: 26
<212> TYPE: PRT
<213> ORGANISM: Artificial Sequence
<220> FEATURE:
<223> OTHER INFORMATION: Synthetic

<400> SEQUENCE: 7

Val Gly Phe Pro Val Ala Ala Val Gly Phe Pro Val Ala Ala His Pro
1               5                   10                  15

Leu Ser Lys His Pro Tyr Trp Ser Gln Pro
            20                  25
```

```
<210> SEQ ID NO 8
<211> LENGTH: 40
<212> TYPE: PRT
<213> ORGANISM: Artificial Sequence
<220> FEATURE:
<223> OTHER INFORMATION: Synthetic

<400> SEQUENCE: 8

Val Gly Phe Pro Val Ala Ala Val Gly Phe Pro Val Ala Ala His Pro
1               5                   10                  15

Leu Ser Lys His Pro Tyr Trp Ser Gln Pro Ala Ala His Pro Leu Ser
            20                  25                  30

Lys His Pro Tyr Trp Ser Gln Pro
        35                  40

<210> SEQ ID NO 9
<211> LENGTH: 29
<212> TYPE: PRT
<213> ORGANISM: Artificial Sequence
<220> FEATURE:
<223> OTHER INFORMATION: Synthetic

<400> SEQUENCE: 9

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic

<400> SEQUENCE: 10

Met Leu Ser Asn Leu Arg Ile Leu Leu Asn Lys Ala Ala Leu Arg Lys
1               5                   10                  15

Ala His Thr Ser Met Val Arg Asn Phe Arg Tyr Gly Lys Pro Val Gln
            20                  25                  30

Cys

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

Met Leu Ser Leu Arg Gln Ser Ile Arg Phe Phe Lys Pro Ala Thr Arg
1               5                   10                  15

Thr Leu

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Arg Gln Ile Lys Ile Trp Phe Gln Asn Arg Arg Met Lys Trp Lys Lys
1               5                   10                  15
```

```
<210> SEQ ID NO 13
<211> LENGTH: 34
<212> TYPE: PRT
<213> ORGANISM: Artificial Sequence
<220> FEATURE:
<223> OTHER INFORMATION: Synthetic

<400> SEQUENCE: 13

Met Phe Ser Tyr Leu Pro Arg Tyr Pro Leu Arg Ala Ala Ser Ala Arg
1               5                   10                  15

Ala Leu Val Arg Ala Thr Arg Pro Ser Tyr Arg Ser Ala Leu Leu Arg
            20                  25                  30

Tyr Gln

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Met Ala Ala Trp Met Arg Ser Leu Phe Ser Pro Leu Lys Lys Leu Trp
1               5                   10                  15

Ile Arg Met His
            20

<210> SEQ ID NO 15
<211> LENGTH: 13
<212> TYPE: PRT
<213> ORGANISM: Artificial Sequence
<220> FEATURE:
<223> OTHER INFORMATION: Synthetic

<400> SEQUENCE: 15

Met Lys Leu Leu Trp Arg Leu Ile Leu Ser Arg Lys Trp
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Met Trp Trp Arg Arg Ser Arg Thr Asn Ser Leu Arg Tyr Thr
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic

<400> SEQUENCE: 17

Met Leu Phe Arg Leu Arg Arg Ser Val Arg Leu Arg Gly Leu Leu Ala
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 18

Met Trp Thr Leu Gly Arg Arg Ala Val Ala Gly Leu Leu Ala Ser Pro
1               5                   10                  15

Ser Pro Ala Gln
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Arg Arg Ile Val Val Leu His Gly Tyr Gly Ala Val Lys Glu Val Leu
1               5                   10                  15

Leu Asn His Lys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic

<400> SEQUENCE: 20

Met Leu Ser Leu Arg Gln Asp Ile Arg Phe Phe Lys Pro Ala Thr Arg
1               5                   10                  15

Thr Leu Cys Ser Ser Arg
            20

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Arg Pro Leu Ala Leu Trp Arg Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Glu Ser Pro Ala Tyr Tyr Thr Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Asp Pro Arg Ser Phe Leu
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Pro Pro Arg Ser Phe Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Arg Leu Gln Leu Lys Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: ACETYLATION

<400> SEQUENCE: 26

Arg Leu Gln Leu Lys
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 27

Arg Xaa Xaa Arg
1

<210> SEQ ID NO 28
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is Lys or Arg

<400> SEQUENCE: 28

Arg Xaa Xaa Arg
1
```

<210> SEQ ID NO 29
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is Glu or Asp

<400> SEQUENCE: 29

Ile Xaa Gly Arg
1

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Leu Val Pro Arg Gly Ser
1               5

<210> SEQ ID NO 31
<211> LENGTH: 13
<212> TYPE: DNA
<213> ORGANISM: Artificial Sequence
<220> FEATURE:
<223> OTHER INFORMATION: Synthetic

<400> SEQUENCE: 31
ccgccaagaa gcg                                                           13

<210> SEQ ID NO 32
<211> LENGTH: 100
<212> TYPE: DNA
<213> ORGANISM: Artificial Sequence
<220> FEATURE:
<223> OTHER INFORMATION: Synthetic

<400> SEQUENCE: 32
gcgtgcacac gcgcgtagac ttccccgca agtcactcgt tagcccgcca agaagcgacc         60
cctccggggc gagctgagcg gcgtggcgcg ggggcgtcat                              100

<210> SEQ ID NO 33
<211> LENGTH: 101
<212> TYPE: DNA
<213> ORGANISM: Artificial Sequence
<220> FEATURE:
<223> OTHER INFORMATION: Synthetic

<400> SEQUENCE: 33
acgtgcatac gcacgtagac attccccgct tcccactcca aagtccgcca agaagcgtat        60
cccgctgagc ggcgtggcgc gggggcgtca tccgtcagct c                            101

<210> SEQ ID NO 34
<211> LENGTH: 58
<212> TYPE: DNA
<213> ORGANISM: Artificial Sequence
<220> FEATURE:
<223> OTHER INFORMATION: Synthetic

```
<400> SEQUENCE: 34
acttcccccg caagtcactc gttagcccgc caagaagcga cccctccggg gcgagctg        58

<210> SEQ ID NO 35
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: At least one and up to four may be present
<220> FEATURE:
<221> NAME/KEY: misc_feature
<222> LOCATION: (5)..(5)
<223> OTHER INFORMATION: Xaa is Ser or Ala
<220> FEATURE:
<221> NAME/KEY: misc_feature
<222> LOCATION: (6)..(20)
<223> OTHER INFORMATION: "Gly(1-4)-Ser/Ala" may or may not be present

<400> SEQUENCE: 35

Gly Gly Gly Gly Xaa Gly Gly Gly Gly Xaa Gly Gly Gly Gly Xaa Gly
1               5                   10                  15

Gly Gly Gly Xaa
            20
```

COMPOSITIONS AND METHODS FOR TREATING DISEASES BY INHIBITING EXOSOME RELEASE

FIELD

The present disclosure generally relates to compositions and methods for medical treatment, and in particular, to methods for treating cancers and infectious diseases by inhibiting exosome release.

BACKGROUND

Membrane exosomes are spherical membrane microvesicles, generally less than 200 nm in diameter. The exosomes are composed of a lipid bilayer containing a cytosolic fraction. Particular membrane vesicles are more specifically produced by cells, from intracellular compartments through fusion with the cytoplasmic membrane of a cell, resulting in their release into the extracellular biological fluids of an organism or into the supernatant of cells in culture. These exosomes may be released in a number of ways. The classical secretory pathway processes mainly traditional membrane signals bearing receptors through the endoplasmic Reticulum (ER) membrane (Lee et al., (2004) Annu. Rev. Cell Dev. Biol. 20, 87-123).

Secretory proteins are packaged into transport vesicles, delivered to the Golgi apparatus, and eventually released into the extracellular space. Alternatively, nonclassical secretory pathways mediate translocation of cytosolic, non-signal bearing molecules into the extracellular space (Lippincott-Schwartz et al., (1989) Cell 56, 801-813; and Misumi et al., (1986) J. Biol. Chern. 261, 11398-11403). Two of these involve intracellular vesicles of the endocytic membrane system, such as secretory lysosomes (Muesch et al., (1990) Trends Biochem. Sci. 15, 86-88) and exosomes (Johnstone et al., (1987) J. Biol. Chem. 262, 9412-9420), the latter ones being internal vesicles of late endosomes or multi vesicular bodies (MVB). Lysosomal contents gain access to the exterior of cells when specialized endocytic structures such as secretory lysosomes of cytotoxic T lymphocytes, fuse with the plasma membrane. Lumenal contents of late endocytic structures are released into the extracellular space when MVBs fuse with the plasma membrane resulting in release of the internal multi vesicular endosomes into the extracellular space (called exosomes) along with their cargo molecules. Other nonclassical pathways involve direct translocation of cytosolic factors across the plasma membrane using protein conducting channels or a process called membrane blebbing (Nickel, W. (2005) Traffic. 6, 607-614). Membrane blebbing is characterized by shedding of plasma membrane-derived microvesicles into the extracellular space.

Exosome release has been demonstrated from different cell types in varied physiological contexts. It has been demonstrated that tumor cells secrete exosomes, such as exosomes in a regulated manner, which can carry tumor antigens that can be presented to antigen presenting cells (Patent Application No. WO99/03499). In addition, FasL or TNF containing exosomes are known to cause a state of immune privilege/immune suppression which can promote tumor growth. Similarly, virus-infected cells, including those infected by HIV are known to release Nef-containing exosomes (Guy et al., (1990) Virology 176, 413-425; and Campbell et al., (2008) Ethn. Dis. 18, S2-S9), which serve to suppress the immune system allowing HIV to survive. Exosome secretion has been shown to utilize the same endosomal trafficking pathway involved in virion release from infected cells (Sanfridson et al., (1997) Proc. Natl. Acad. Sci. U.S.A 94, 873-878; and Esser et al., (2001) J Virol. 75, 6173-6182).

Tumors are known to release large numbers of exosomes, which can cause immune suppression through immune cell killing or dysregulation, thereby promoting a state of immunosuppression that allows for rapid tumor growth (Lindner K. et al., 2015, Salido-Guadarrama I. et al., 2014). Similarly, HIV infections result in high numbers of exosomes, which appears to contribute to a state of immune privilege/suppression which ultimately could lead to Acquired Immune Deficiency Syndrome (AIDS).

The exosome secretion pathway serves a dual function in both regulation of the cancer homeostasis, the immune system and virion release of infected cells. In view of the foregoing, there is a need in the art for compositions and effective methods of treatment for inhibiting exosome release.

SUMMARY

One aspect of the present disclosure relates to a multipartite peptide that inhibits the release of exosomes from cells. The peptide contains at least one secretion modifying region (SMR) peptide from HIV-1 Nef and at least one Clusterin (Clu)-binding peptide (Clu-BP).

In one embodiment, the peptide contains at least one SMR peptide sequence, such as VGFPV (SEQ ID NO: 1) or VGFPVAAVGFPV (SEQ ID NO:2), and at least one Clu-BP peptide sequence selected from the group consisting of HPLSKHPYWSQP (SEQ ID NO:3), NTYWSQLLHFQT (SEQ ID NO:4) and SHALPLTWSTAA (SEQ ID NO:5). In one embodiment, the peptide has an SMR peptide motif at its N-terminal end and a Clu-BP peptide motif at its C-terminal end. In another embodiment, the peptide has a Clu-BP peptide at its N-terminal end and an SMR peptide at its C-terminal end.

In certain embodiments, the peptide has a plurality of SMR peptide motifs separated by a suitable spacer peptide, a plurality of Clu-BP peptide motifs separated by a suitable spacer peptide, or both.

In a particular embodiment, the peptide comprises an amino acid sequence selected from the group consisting of VGFPVAAVGFPVHPLSKHPYWSQP (SEQ ID NO:6), VGFPVAAVGFPVAAHPLSKHPYWSQP (SEQ ID NO:7), VGFPVAAVGFPVAAHPLSKHPYWSQPAAHPLSKHPYWSQP (SEQ ID NO:8).

In another embodiment, a pharmaceutical composition comprises a multipartite peptide in accordance with the present disclosure and a pharmaceutically acceptable carrier.

Another aspect relates to polynucleotides and expression vectors encoding the multipartite peptides described herein.

In a further aspect, a method for treating cancer or an infectious disease comprises administering to a subject in need of such treatment an effective amount of a multipartite peptide in accordance with the present disclosure.

In another aspect, a method for treating AIDS comprises administering to a subject in need of such treatment an effective amount of a multipartite peptide in accordance with the present disclosure.

BRIEF DESCRIPTION OF THE DRAWINGS

The above and other objects and advantages of the application will be apparent upon consideration of the following detailed description, taken in conjunction with the accompanying figures and paragraphs. The following are brief descriptions of the drawings herein, which illustrate certain aspects and embodiments of the present application, but are not considered limiting in any way.

DETAILED DESCRIPTION

Figure 1:
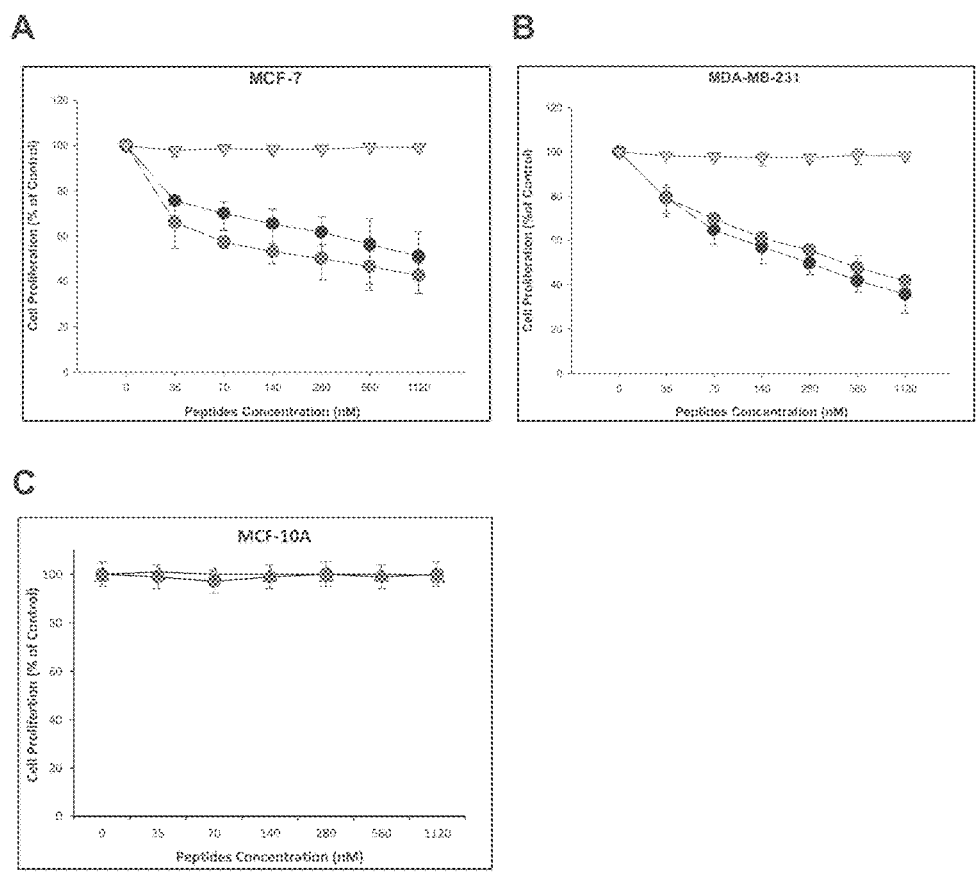
FIG. 1 shows that SMRwt peptide antagonists inhibit proliferation of MCF-7 and MDA-MB-231 breast cancer cells but not non-tumorigenic cells. Cells were incubated with peptides at varying dosage (0-1120 nM) for 24 hr, after which proliferation was measured by MTT assay. Results of three independent experiments are shown. Panel A: Proliferation of MCF-7 breast cancer cells. Panel B: Proliferation of MDA-MB-231 breast cancer cells. Panel C: Proliferation of non-tumorigenic MCF-10A cells. Red dots indicate PEG-SMRwt peptide, black dots indicate PEG-SMRwt-CLU peptide, and green triangles indicate PEG-SMRmut peptide.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein. Further, where the phrases "in some embodiments . . . " or "in certain embodiments . . . " are used, the present disclosure should be construed as embracing combinations of any of the features defining the different embodiments described herein, unless the features are not combinable with one another, are mutually exclusive, or are expressly disclaimed herein.

Definitions

As used herein, the terms "treat" and "treatment" refer to the amelioration of one or more symptoms associated with a disease, such as cancer or an infectious disease; prevention or delay of the onset of one or more symptoms of the disease; and/or lessening of the severity or frequency of one or more symptoms of the disease.

The term "cancer" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancers of the brain, bladder, breast, cervix, colon, head and neck, kidney, lung, non-small cell lung, mesothelioma, ovary, prostate, stomach and uterus, leukemia, and medulloblastoma.

The term "infectious diseases" includes those pathologic conditions that arise from viruses, bacteria, fungi and/or parasites that invade and disrupt the normal function of the mammalian body. Pages 3-147 of the Merck Manual 13th Edition describe some of these conditions and they are incorporated herein by reference.

The phrases "to a patient in need thereof", "to a patient in need of treatment" or "a subject in need of treatment" includes subjects, such as mammalian subjects, that would benefit from administration of the multipartite peptide of the present disclosure for treatment of a cell proliferative disorder.

The terms "therapeutically effective amount", "pharmacologically effective amount", and "physiologically effective amount" are used interchangeably to mean the amount of a multipartite peptide that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same disease as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

A "small molecule" refers to an organic or inorganic molecule that is not a polymer, that has medicinal activity, and that has a molecular weight less than 1 kDa. The term encompasses most medicinal compounds termed "drugs" other than protein or nucleic acids, although a small molecule peptide or nucleic acid analog can be considered a "small molecule". Small molecules drugs can be derived synthetically, semi-synthetically (i.e., from naturally occurring precursors), or biologically. As used herein, the phrase "large molecule" refers to a polymeric protein- or nucleic acid-based product having a molecular weight greater than 1 kDa.

Peptides

One aspect of the present disclosure relates to a multipartite peptide that inhibits the release of exosomes from cells. In one embodiment, the peptide comprises at least one secretion modifying region (SMR) peptide from HIV-1 Nef and at least one Clusterin (Clu)-binding peptide (Clu-BP).

In a particular embodiment, the SMR peptide comprises the amino acid sequence VGFPV (SEQ ID NO: 1) or VGFPVAAVGFPV (SEQ ID NO: 2), and at least one Clu-BP peptide selected from the group consisting of HPL-SKHPYWSQP (SEQ ID NO:3), NTYWSQLLHFQT (SEQ ID NO:4) and SHALPLTWSTAA (SEQ ID NO:5) as described in U.S. Patent Publication No. 2012/0121507.

In one embodiment, the peptide comprises an SMR peptide at the N-terminal end and an Clu-BP peptide at the C-terminal end. In another embodiment, the peptide comprises a Clu-BP peptide at the N-terminal end and an SMR peptide at the C-terminal end.

In certain embodiments, the peptide comprises at least two SMR peptides separated by a spacer peptide, at least two Clu-BP peptides separated by a spacer peptide, or both.

In certain particular embodiments, the peptide comprises an amino acid sequence selected from the group consisting of VGFPVAAVGFPVHPLSKHPYWSQP (SEQ ID NO:6), VGFPVAAVGFPVAAHPLSKHPYWSQP (SEQ ID NO:7), VGFPVAAVGFPVAAHPLSKHPYWSQPAAHPLSKHPY-WSQP (SEQ ID NO:8).

In certain embodiments, the multipartite peptide of the present invention further comprises one or more spacers between one or more functional domains within the multipartite peptide. The spacer is designed to facilitate the independent folding of each domain relative to one another, ensure that the individual domains in the peptide do not interfere with one another or with the SMR peptide and/or increase the flexibility of the protein and facilitate adoption of an extended conformation. In some embodiments, the spacer comprises 1 to 50 amino acids, preferably 2 to 10 amino acids.

In some embodiments, the spacer includes one or more a glycine and/or serine residues to force the spacer to adopt a loop conformation, because the absence of a B-carbon permits the polypeptide backbone to access dihedral angles that are energetically forbidden for other amino acids. In addition, spacers comprising glycine and/or serine have a high freedom degree for linking of two peptides, i.e., they enable the fused proteins to fold and produce functional proteins. Other residues that can enhance stability and folding include the amino acids alanine, proline, lysine, and combinations thereof. In one embodiment, the spacer is an Ala-Ala dipeptide linker. In another embodiment, the spacer has the formula [(Gly)n-Ser/Ala]m (SEQ ID N0:35), where n is from 1 to 4, inclusive, and m is from 1 to 4, inclusive.

In some embodiments, the multipartite peptide further comprises a cell penetrating peptide (CPP) domain. A CPP domain enhances the uptake of the multipartite peptide into eukaryotic cells. Exemplary CPP domains for use in the present application include, but are not limited to, HIV $TAT_{49-57}$ peptide, HIV $TAT_{48-60}$ peptide, low molecular weight protamine (LMWP) peptide; Chariot™, also known as Pep-1 (Morris et al., *Nat. Biotechnol.*, 19:1173-1176, 2001); $Antp_{43-58}$ peptide, MPG (HIV Gp41-SV40 NLS), SAP, MPG R9, MAP, K-FGF, Penetratin, Buforin II, Transportan, Ku70, Prion, pVEC, Pep-1-K, Pep-7, HN-1, TP10, and CP26 (See e.g., Joliot et al., *Nature Cell Biol.*, 6(3): 189-196, 2004 and Heitz et al., *Br. J. Pharmacol.*, 157:195-206, 2009).

In certain particular embodiments, the multipartite peptide further includes a mitochondrial penetrating sequence or a mitochondrial targeting signal sequence to facilitate uptake of the multipartite peptides into the mitochondria where mortalin is localized. Exemplary mitochondrial targeting sequences include the presequence peptide described in U.S. Patent Publication 2004/0192627, including the nuclear-encoded human cytochroine c oxidase (COX) subunit VIII (MSVLTPLLLRGLTGSARRLPVPRAKIHSL (SEQ ID NO:9)); the amino-terminal leader peptide of the rat ornithine transcarbamylase (OTC) (MLSNLRILLNKAAL- RKAHTSMVRNFRYGKPVQC (SEQ ID NO:10)), the presequence of cytochrome oxidase subunit IV (MLSLRQSIRFFKPATRTL (SEQ ID NO:11)), and an Antennapedia α-helical domain, such as RQIKIWFQN-RRMKWKK (SEQ ID NO:12); various mitochondrial targeting peptides described in U.S. Patent Publication No. 2014/0196172, including N-terminal mitochondrial targeting peptides, MFSYLPRYPLRAASARALVRATRPSYR-SALLRYQ (SEQ ID NO:13), MAAWMRSLFSPLKKL-WIRMH (SEQ ID NO:14), MKLLWRLILSRKW (SEQ ID NO:15), MWWRRSRTNSLRYT (SEQ ID NO:16), and MLFRLRRSVRLRGLLA (SEQ ID NO:17); and the N-terminal mitochondrial targeting peptide MWTLGRRAVAGL-LASPSPAQ (SEQ ID NO:18) as described in U.S. Patent Publication No. 2016/0237129. Exemplary mitochondrial targeting signal peptide sequences directing proteins or peptides to the mitochondria include RRIVVLHGY-GAVKEVLLNHK (SEQ ID NO:19), amino acids 74-95 of Rat Cytochrome P450 2E1 (CYP2E1), the cleavable prepiece from the yeast cytochrome c oxidase IV precursor (MLSLRQDIRFFKPATRTLCSSR (SEQ ID NO:20)), the mitochondrial-targeting signal from the PB2 protein of influenza viruses, the import signal contained within heme lyases, and the leader peptide of the mitochondrial matrix enzyme ornithine transcarbamylase (OTC) as described in U.S. Patent Publication No. 2014/0142121.

In some embodiments, the multipartite peptide may include a targeting domain for targeting the peptide to specific types of cells, including tumor cells, virally-infected cells and the like. The targeting domain may comprise a peptide fused to the multipartite peptide or it may be non-peptide-based domain chemically conjugated to or covalently attached thereto. Exemplary targeting domains include a peptides, small molecules, ligands, antibody fragments, and aptamers. In addition, a targeting domain may be a small molecule (e.g., folate, adenosine, purine) or a large molecule (e.g., peptide or antibody) that specifically binds to a desired target cell of interest. In some embodiments, the targeting domain is present at the C-terminal end of the multipartite peptide. In other embodiments, the targeting domain is present at the N-terminal end of the multipartite peptide.

In some embodiments, the multipartite peptide may be linked to an immunoglobulin Fc region. The Fc region can enhance stability and in vivo half-life and can facilitate recruitment of Fc receptor-bearing natural killer cells, macrophages, neutrophils, and mast cells, which can stimulate phagocytic or cytotoxic cells to destroy microbes or infected cells by antibody-mediated phagocytosis or antibody-dependent cell-mediated cytotoxicity. When using antibody-derived targeting agents or Fc regions, these domains are preferably "humanized" using methodologies well known to those of skill in the art.

The multipartite peptide encoded in the expression vector may further include a cleavage recognition sequence for proteolytic or endopeptidase cleavage sequence between one or more functional domains. Incorporation of endopeptidase cleavage recognition sequences can facilitate site specific cleavage by a suitable endopeptidase present in a eukaryotic or mammalian cell, such as asparagine endopeptidase, Factor Xa, furin, thrombin, cathepsin B, plasmin, and various matrix metalloproteinases (MMPs), such as MMP2, MMP7, MMP9, or MMP14. Placement of a suitable endopeptidase cleavage recognition sequence can serve to liberate an attached PEG moiety and/or liposomal moiety linked to the peptide, or liberate one or more peptide domains from one another so that one or more these peptide domains can function independently of one another in e.g., their targeted site.

Asparagine endopeptidase, also known as legumain, is a lysosomal cysteine protease that cleaves protein substrates on the C-terminal side of asparagine, such as Asn-Asp. Sequences cleavable by MMP2, MMP7, MMP9, or MMP14 include PLGLAG, PLG-C(me)-AG, RPLALWRS (SEQ ID NO:21), ESPAYYTA (SEQ ID NO:22), DPRSFL (SEQ ID NO:23), PPRSFL (SEQ ID NO:24), RLQLKL (SEQ ID NO:25), and RLQLK(Ac) (SEQ ID NO:26). Cathepsin B is a tumor associated protease that can act upon the dipeptide sequences valine-citrulline and Phe-Lys. Furin cleaves the recognition sequence Arg-X-X-Arg (SEQ ID NO:27), more preferably Arg-X-(Lys/Arg)-Arg (SEQ ID NO:28). Factor Xa cleaves after the arginine residue in its preferred cleavage site Ile-(Glu or Asp)-Gly-Arg (SEQ ID NO:29) and will sometimes cleave at other basic residues, depending on the conformation of the protein substrate. The most common secondary site, among those that have been sequenced, is Gly-Arg. Thrombin preferentially cleaves between Arg and Gly residues in e.g., the sequence LVPRGS (SEQ ID NO:30).

The multipartite peptide of the present disclosure may be chemically modified using one or more methods including, but not limited to, amidation, acetylation (including N-terminal acetylation), carboxylation, glycosylation, methylation (e.g., substitution of α-hydrogens with methyl groups), carbonylation, phosphorylation, PEGylation, dimerization, addition of interchain and/or intrachain disulfide bonds, addition of trans olefin, derivatization by known protecting/blocking groups, circularization, substitution with D amino acids, linkage to an antibody molecules or other cellular ligands, etc.

The multipartite peptides of the present disclosure can be modified to contain additional nonproteinaceous moieties that are known in the art and are readily available. Preferably, the moieties suitable for derivatization of the protein are water soluble polymers. Non-limiting examples of water soluble polymers include, but are not limited to, polyethylene glycol (PEG), polyvinyl alcohol (PV A), copolymers of ethylene glycol/propylene glycol, carboxymethylcellulose, dextran, polyvinyl alcohol, polyvinylpyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polyproylene glycol (PPG) homopolymers, polypropylene oxide/ethylene oxide co-polymers, polyoxyethylated polyols (e.g., glycerol; POG), polyvinyl alcohol, and mixtures thereof. Polyethylene glycol propionaldehyde may have advantages in manufacturing due to its stability in water.

Additional modifications include, for example, point mutations, insertions, deletion, truncation, and backbone substitutions, such as NH to $NCH_3$, In addition, the peptide may be modified by the insertion of one or more D amino acids. Further, proline analogs in which the ring size of the proline residue is changed from 5 members to 4, 6, or 7 members can be employed. Cyclic groups can be saturated or unsaturated, and if unsaturated, can be aromatic or non-aromatic.

The multipartite peptides may include modifications to, including incorporation of any of the functional domains described herein at the N-terminal end of the peptide, the C-terminal end of the peptide, or both. Alternatively, or in addition, modifications at the N-terminal end may include an acetylated (Ac) residue and/or an amidated ($NH_2$) residue at the C-terminal end. Where the C-terminus is amidated, the carboxylic acid of the amino acid is converted to an amide, i.e., $NH_2$—$CH_2$—$C(O)$—$NH_2$.

The multipartite peptide may further contain one or more covalently attached functional groups, preferably attached to either or both of the N and C termini of the polypeptide. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, small molecule drugs, proteins, enzymes, enzymatic substrates, etc. Alternatives to cya are also known to those of skill in the art. For stabilizing and/or blocking, e.g., cya may be replaced with an alky group such as methyl or ethyl, which are known to be conveniently positioned onto a —COOH group.

N-terminal modifications additionally may include, but are not limited to, methylation (i.e., —$NHCH_3$ or —$NH(CH_3)_2$), adding a 1-amino-cyclohexane-carboxylic acid moiety (Chex); and adding a carbobenzoyl group, or blocking the amino terminus with any blocking group containing a carboxylate functionality defined by RCOO—, where R is selected from the group consisting of naphthyl, acridinyl, steroidyl, and similar groups.

A derivatizing group, including, but not limited to, a sulfhydryl-containing group or moiety may be positioned at the C-terminus of the multipartite peptide, even when it is not coupled to another chemical moiety. In one embodiment, the C-terminal end may be modified with a cysteamide group (—NH—$CH_2$—$CH_2$—SH), which can allow further coupling to drugs. A cysteamide group is compatible with the peptide synthesis using the Fmoc strategy and leads to a C-terminal protected peptide. Alternatively, the peptide can include a C-terminal cysteine residue containing a sulfhydryl (—SH) group that can be optionally utilized for conjugation to other moieties. In another embodiment, the C-terminal end includes a 2,4-diamino-butyric acid (DAB) moiety. C-terminal modifications may further include replacing the free acid with a carboxamide group or forming a cyclic lactam at the carboxy terminus to introduce structural constraints.

Naturally occurring side chains of the 20 genetically encoded amino acids (or D amino acids) may be replaced with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine; N-(4-aminobutyl)-glycine having a lysine side chain attached to the "N-terminus" and aminopropyl or aminoethyl groups attached to the amino group of glycine; (2) Non-naturally occurring amino acids with no net charge and sidechains similar to arginine, such as citrulline, with or without methylene groups; (3) non-standard non-naturally occurring amino acids with OH (e.g., serine), such as, homoserine, hydroxyproline, hydroxyvaline, and penicillamin; (4) proline derivatives, such as, D-Pro, including 3,4-dehydroproline, pyroglutamine, proline with fluorine substitutions on the ring, 1,3-thiazolidine-4-carboxylic acid; (5) Histidine derivative, such as beta-(2-thienyl)-alanine; or (6) alkyl derivatives, such as 2-aminobutyric acid, norvaline, norleucine, homoleucine, and alpha-aminoisobutyric acid.

In other embodiments, the C-terminal carboxyl group or a C-terminal ester may be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

In other embodiments, the multipartite peptide of the present disclosure is cyclized or includes a desamino or descarboxy residue at the peptide termini so that there are no terminal amino or carboxyl groups. This can decrease susceptibility to proteases and/or to restrict the conformation of the peptide. C-terminal functional groups of the compounds of the present disclosure include amide, amide lower alkyl, amide di(lower alkyl), lower alkoxy, hydroxy, and carboxy, and the lower ester derivatives thereof, and the pharmaceutically acceptable salts thereof. The multipartite peptide may be cyclized by adding an N and/or C terminal cysteine and cyclizing the peptide through disulfide linkages or other side chain interactions.

In one preferred embodiment, the multipartite peptide (or pharmaceutical composition thereof) has the structure A-B-C-D, where A is a PEG, such as a 10 kD PEG; B is a peptide cleavage linker sequence for an endopeptidase, such as asparagine endopeptidase; C is an SMR-containing peptide sequence, such as VGFPVAAVGFPV (SEQ ID NO:2); and D is a Clu-BP peptide sequence, such as HPLSKHPYWSQP (SEQ ID NO:3).

The multipartite peptides of the present disclosure may be administered as naked peptides with or without PEG moieties, or they may be incorporated into suitable carriers, such as liposomes, nanoparticles, hydrogels, microcapsules, viruses or bacteriophages, or virus-like particles (VLPs).

Peptide-Encoding Polynucleotides

Another aspect of the present disclosure relates to a polynucleotide encoding any of the multipartite peptides described herein. In one embodiment, the polynucleotide is an expression vector. As used herein, the term "expression vector" refers to a non-viral or a viral vector that comprises a polynucleotide encoding the multipartite peptide of the present disclosure in which the peptide coding sequences are operably linked to regulatory sequences sufficient for expressing the peptide in a cell. One type of non-viral vector is a "plasmid", which includes a circular double-stranded DNA loop into which additional DNA segments can be ligated. In the present specification, "plasmid" and "vector" can be used interchangeably as the plasmid is the most commonly used form of vector.

The regulatory sequences may be selected on the basis of the host cells to be used for expression, such that the design of the expression vector and inclusion of regulatory sequences depends on such factors as the choice of the host cell to be transformed, the level of expression of protein desired, whether the peptide is to be secreted into the extracellular milieu and the like. The expression vectors of the invention can be introduced into host cells to direct the expression of the multipartite peptide of the present disclosure in vitro for production purposes or in vivo for therapeutic purposes.

As used herein, the terms "control sequences" or "regulatory sequences" refer to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is "operably linked" to another nucleic acid sequence when the former is placed into a functional relationship with the latter. For example, in certain embodiments, the expression vector encodes a pre-sequence or signal peptide that is operably linked to the peptide coding sequences for expression as a preprotein that participates in the secretion of the polypeptide. In addition, a promoter or enhancer is said to be operably linked to a coding sequence if it affects the transcription of the sequence and a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking these sequences may be accomplished by ligation at convenient restriction sites or by the use of synthetic oligonucleotide adaptors, primers, and/or linkers are used in accordance with conventional practices in the art.

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In certain embodiments, the expression vector is engineered to direct expression of the peptide ubiquitously or preferentially in a particular cell type (e.g., tissue-specific regulatory elements are used to express the polynucleotide). Thus, in certain embodiments, expression of the peptide is under the control of a tissue specific or ubiquitous promoter, such as the CMV promoter or a CMV-chicken beta-actin hybrid (CAG) promoter. In other embodiments, a tissue specific or tumor-specific promoter may be used. Exemplary tissue-specific regulatory elements are known in the art and may include liver-specific promoter (e.g., albumin promoter), lymphoid-specific promoters, epithelial cell-specific promoters, promoters of T cell receptors and immunoglobulins, neuron-specific promoters (e.g., the neurofilament promoter), pancreas-specific promoters (e.g., insulin promoter), and mammary gland-specific promoters (e.g., milk whey promoter). Developmentally-regulated promoters (e.g., the α-fetoprotein promoter) are also encompassed.

In certain embodiments, the multipartite expression construct may be linked to a mitochondrial targeting peptide or leader sequence to facilitate uptake of the expression construct into mitochondrial cells as described in U.S. Patent Publication No. 20040192627. Conventional protocols may be used to conjugate the expression construct with the mitochondrial targeting peptide, e.g., pGeneGrip™ technology (Genlantis/Gene Therapy Systems, Inc., San Diego, Calif.). Alternatively, the multipartite peptide coding sequence may be fused to a mitochondrial targeting sequence to direct translocation of the expressed peptide into mitochondria as described above.

In other embodiments, the multipartite peptide coding sequence may be fused to a mitochondrial penetrating moiety or mitochondrial targeting signal sequence as described above. Exemplary nucleic acids that act as mitochondrial penetrating moieties (such as those described in U.S. Pat. No. 5,569,754) include e.g., CCGCCAAGAAGCG (SEQ ID NO:31), GCGTGCACACGCGCGTAGACTTCCCCCGCAAGTCACTCGTTAGCCCGCCAAGAAGC GACCCCTCCGGGGCGAGCTGAGCGGCGTGGCGCGGGGGCGTCAT (SEQ ID NO:32), ACGTGCATACGCACGTAGACATTCCCCGCTTCCCACTCCAAAGTCCGCCAAGAAGCG TATCCCGCTGAGCGGCGTGGCGCGGGGGCGTCATCCGTCAGCTC (SEQ ID NO:33) or ACTTCCCCCGCAAGTCACTCGTTAGCCCGCCAAGAAGCGACCCCTCCGGGGCGAGCT G (SEQ ID NO:34).

In some embodiments, the multipartite peptide coding sequence may be fused to a signal peptide domain for secretion of the peptide from cells expressing the peptide. The signal peptide sequence is removed from the mature peptide as the mature peptide is secreted from the cell. Since a given signal peptide sequence can affect the level of peptide expression, a peptide-encoded polynucleotide may include any one of a variety of different N-terminal signal peptide sequences known in the art.

In some embodiments, the expression vector is a viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

Non-viral expression vectors can be utilized for non-viral gene transfer, either by direct injection of naked DNA or by encapsulating the multipartite peptide-encoding polynucleotides in liposomes, nanoparticles, hydrogels, microcapsules, or virus-like particles. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Pharmaceutical Compositions

In some embodiments, a pharmaceutical composition comprises a multipartite peptide comprising at least one SMR peptide from HIV-1 Nef, at least one Clusterin (Clu)-binding peptide (Clu-BP) and a pharmaceutically acceptable carrier. In addition, the multipartite peptide may include any of the above described modification.

In another embodiment, a pharmaceutical composition comprises an expression vector encoding a multipartite peptide comprising at least one SMR peptide from HIV-1 Nef, at least one Clusterin (Clu)-binding peptide (Clu-BP) and a pharmaceutically acceptable carrier, whereby the encoded peptide is designed to include any of the above described modifications.

As used herein, the term "pharmaceutically acceptable" refers to a molecular entity or composition that does not produce an adverse, allergic or other untoward reaction when administered to an animal or a human, as appropriate. The term "pharmaceutically acceptable carrier", as used herein, includes any and all solvents, solubilizers, fillers, stabilizers, surfactants, binders, absorbents, bases, buffering agents, excipients, lubricants, controlled release vehicles, diluents, emulsifying agents, humectants, lubricants, gels, dispersion media, coatings, antibacterial or antifungal agents, isotonic and absorption delaying agents, and the like, compatible with pharmaceutical administration. The use of such carriers and agents for pharmaceutically active substances is well-known in the art. See e.g., A. H. Kibbe Handbook of Pharmaceutical Excipients, 3rd ed. Pharmaceutical Press, London, UK (2000).

Exemplary carriers or excipients include but are not limited to, calcium carbonate, calcium phosphate, various sugars, starches, cellulose derivatives, gelatin, polymers such as polyethylene glycols, water, saline, isotonic aqueous solutions, phosphate buffered saline, dextrose, 0.3% aqueous glycine, glycerol, ethanol and the like, as well as combinations thereof. In many cases, it will be preferable to include isotonic agents, for example, sugars, polyalcohols such as mannitol, sorbitol, or sodium chloride in the composition, or glycoproteins for enhanced stability, such as albumin, lipoprotein and globulin. Pharmaceutically acceptable carriers may further comprise minor amounts of auxiliary substances such as wetting or emulsifying agents, preservatives or buffers, which enhance the shelf life or effectiveness of the therapeutic agents. In certain embodiments, the pharmaceutically acceptable carrier comprises serum albumin.

Formulation characteristics that can be modified include, for example, pH and osmolality. For example, it may be desired to achieve a formulation that has a pH and osmolality similar to that of human blood or tissues to facilitate the formulation's effectiveness when administered parenterally.

Buffers are useful in the present invention for, among other purposes, manipulation of the total pH of the pharmaceutical formulation (especially desired for parenteral administration). A variety of buffers known in the art can be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present invention include sodium or potassium buffers, including sodium phosphate, potassium phosphate, sodium succinate and sodium citrate.

Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%).

In one embodiment, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present invention include a pH of about 2.0 to a pH of about 12.0.

In some embodiments, it will also be advantageous to employ surfactants in the presently disclosed formulations, where those surfactants will not be disruptive of the drug-delivery system used. Surfactants or anti-adsorbants that prove useful include polyoxyethylenesorbitans, polyoxyethylenesorbitan monolaurate, polysorbate-20, such as Tween-20™, polysorbate-80, polysorbate-20, hydroxycellulose, genapol and BRIJ surfactants. By way of example, when any surfactant is employed in the present invention to produce a parenterally administrable composition, it is advantageous to use it in a concentration of about 0.01 to about 0.5 mg/ml.

Additional useful additives are readily determined by those of skill in the art, according to particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 300 mOsm/kg and achievable by the use of sodium chloride in concentrations of about 6.5 to about 7.5 mg/ml with a sodium chloride concentration of about 7.0 mg/ml being particularly effective.

Multipartite peptides can be stored as a lyophilized powder under aseptic conditions and combined with a sterile aqueous solution prior to administration. The aqueous solution used to resuspend the peptides can contain pharmaceutically acceptable auxiliary substances as required to approximate physical conditions, such as pH adjusting and buffering agents, tonicity adjusting agents and the like, as discussed above. Alternatively, the multipartite peptides can be stored as a suspension, preferable an aqueous suspension, prior to administration.

In certain preferred embodiments, the multipartite peptide in the pharmaceutical composition is pegylated. PEGylation is a process for covalently attaching polyethylene glycol polymer chains to another molecule, normally a drug or therapeutic peptide/protein. PEGylation can be achieved by incubation of a reactive derivative of PEG with the multipartite peptide. The covalent attachment of PEG to a multipartite peptide can "mask" the multipartite peptide from the host's immune system (reduced immunogenicity and antigenicity), increase the hydrodynamic size (size in solution) of the multipartite peptide which prolongs its circulatory time by reducing renal clearance. PEGylation can also provide water solubility to hydrophobic proteins.

The PEG molecules are typically characterized as having for example from about 2 to about 1000, or from about 2 to about 300 repeating units. For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein as described in U.S. Patent Publication No. 2012/0171115.

PEG, PEO and POE are oligomers or polymers of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Preferred PEGs are monodisperse or polydisperse, preferably monodisperse. The skilled artisan will be aware that PEG can be polydisperse or monodisperse. Polydisperse PEG comprises a mixture of PEGs having different molecular weights. In the case of polydisperse PEGs, reference to a specific molecular weight will be understood to refer to the number average molecular weight of PEGs in the mixture. The size distribution is characterized statistically by its weight average molecular weight (MW) and its number average molecular weight (Mn), the ratio of which is called the polydispersity index (Mw/Mn). MW and Mn are measured, in certain aspects, by mass spectroscopy. Most of the PEG-protein conjugates, particularly those conjugated to PEG larger than 1 KD, exhibit a range of molecular weights due to a 30 polydisperse nature of the parent PEG molecule. For example, in case of mPEG2K (Sunbright ME-020HS, NOF), actual molecular masses are distributed over a range of 1.5-3.0 KD with a polydispersity index of 1.036. Based on the foregoing, the skilled artisan will be aware that monodisperse PEG comprises a mixture of PEGs comprising substantially the same molecular weight. Monodisperse PEGs are commercially available, e.g., from Polypure AS, Norway.

The average or preferred molecular weight of the PEG may range from 500 Da to 200 kDa, from 1 to 100 kDa, from 2 to 50 kDa, from 5 to 25 kDa, or from 5 kDa to 10 kDa, including any integers encompassed within these ranges.

The choice of the suitable functional group for the PEG derivative is based on the type of available reactive group on the molecule that will be coupled to the PEG. For peptides or proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are useful for linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. In other embodiments, the pegylation agents contain branched, Y shaped or comb shaped polymers that show reduced viscosity and lack of organ accumulation.

Various methods are known in the art for conjugating PEGs to peptides or proteins, as describe in U.S. Patent Publication No. 2012/0171115. Conjugation of PEGs may include the use of spacer moieties that are cleavable or non-cleavable. In some embodiments, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety. In the case of PEG, the molecule can be activated to facilitate its binding to amines or imidazoles, a carboxylic group, a hydroxyl group or a sulfhydryl group.

In another example, a decrease in pH causes cleavage of the spacer to thereby release of the compound into a target cell. A decrease in pH is implicated in many physiological and pathological processes, such as endosome trafficking, tumour growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, esters and endopeptidase cleavage recognition sites.

An activated PEG may be used with cyanuric chloride to produce a PEG dichlorotriazine derivative. This derivative can react with multiple functional nucleophilic functional groups, such as lysine, serine, tyrosine, cysteine and histidine. Two widely used forms of PEG used to conjugate to proteins are succinimidyl carbonate PEG and benzotriazole carbonate PEG (BTC-PEG; U.S. Pat. No. 5,560,234). Both of these compounds react preferentially with lysine residues to form carbamate linkages, however are also known to react with hystidine and tyrosine. SC-PEG is slightly more resistant to hydrolysis than BTC-PEG.

Another PEG useful for conjugating to proteins is PEG-propionaldehyde (U.S. Pat. No. 5,252,714). An advantage of this chemistry is that under acidic conditions (about pHS) it is largely selective for N-terminal a-amine thus avoiding potential problems with nonspecific conjugation. An acetal derivative of PEG-propionaldehyde, i.e., PEG-acetaldehyde provides an additional benefit in so far as it provides for longer storage than PEG-propionaldehyde (U.S. Pat. No. 5,990,237).

Active esters of PEG carboxylic acids are probably one of the most used acylating agents for protein conjugation. Active esters react with primary amines near physiological conditions to form stable amides. Activation of PEG-carboxylic acids to succinimidyl active esters is accomplished by reacting the PEG-carboxylic acid with N-hydroxysuccinimide (NHS or HOSu) and a carbodiimide. Exemplary carboxylic acid derivatives of PEG include carboxymethylated PEG (CM-PEG), butanoic acid derivatives and propionic acid derivatives (U.S. Pat. No. 5,672,662). Changing the distance between the active ester and the PEG backbone by the addition of methylene units can dramatically influence reactivity towards water and amines (e.g., by reducing hydrolysis). Alternatively or in addition, hydrolysis can be reduced by introducing an .alpha.-branching moiety to the carboxylic acid.

PEGylation of free cysteine residues in a protein is useful for site-specific conjugation (e.g., using a protein modified to include cysteine residues as described herein). Exemplary PEG derivatives for cysteine conjugation include PEG-maleimide, PEG-vinylsulfone, PEG-iodoacetamide and PEG-orthopyridyl disulfide. Exemplary methods for conjugating PEG to cysteine residues and for conjugation using PEG-vinylsulfone are well known in the art.

U.S. Pat. No. 5,985,263 describes methods for conjugating PEG to the secondary amine group of histidine, which has a lower pKa than the primary amine. An advantage of this approach is that the acyl-histidine bond is not stable meaning that the peptide or protein is slowly released (i.e., the conjugate behaves as a slow release formulation or a pro-drug).

Another approach for PEGylation is to take advantage of a N-terminal serine or threonine, which can be converted to periodate as discussed above. Using this approach, PEG has been conjugated to bioactive proteins (e.g., Gaertner and Offord, 1996). PEG can also be conjugated to carbohydrate groups.

The pharmaceutical composition of the present disclosure is formulated to be compatible with its intended route of administration. Examples of routes of administration include parenteral, e.g., intrathecal, intra-arterial, intravenous, intradermal, subcutaneous, oral, transdermal (topical) and transmucosal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the multipartite peptide in the required amount in an appropriate solvent with one or a combination of ingredients enumerated above, as required, followed by filtered sterilization. Generally, dispersions are prepared by incorporating the multipartite peptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active peptide plus any additional desired ingredient from a previously sterile-filtered solution thereof.

Oral compositions generally include an inert diluent or an edible carrier. They can be enclosed in gelatin capsules or compressed into tablets. The tablets, pills, capsules, troches and the like can contain any of the following ingredients, or compounds of a similar nature, including a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the peptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for controlled or delayed release of the active ingredient. For example, in certain embodiments, the peptides may be delivered from with an enteric coating applied as a barrier to an oral formulation so as to prevent release of the peptides before they reach the small intestine. As used herein, the term "enteric coating" is a coating comprising of one or more polymers having a pH dependent or pH-independent release profile. An enteric coated pill will not dissolve in the acidic juices of the stomach (pH ~3), but they will in the alkaline (pH 7-9) environment present in the small intestine or colon. An enteric polymer coating typically resists releases of the active agents until sometime after a gastric emptying lag period of about 3-4 hours after administration.

Such enteric coatings or barrier coatings are also used to protect acid-unstable peptides from the stomach's acidic exposure, delivering them instead to a basic pH environment (intestine's pH 5.5 and above) where they do not degrade and can mediate their desired action. An oral formulation may comprise a plurality of barrier coatings comprising a variety of different materials to facilitate release in a temporal manner. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone) or a coating based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, the formulation may additionally include a time delay material such as glyceryl monostearate or glyceryl distearate.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to tumor antigens or viral antigens) can also be used as pharmaceutically acceptable carriers.

It is especially advantageous to formulate the peptide compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Methods of Treatment

In another aspect, the present disclosure provides methods for treating cancers and infectious diseases. In some embodiments, the present application relates to a method for treating cancer. The method comprises the step of administering to a subject in need thereof an effective amount of a pharmaceutical composition comprising a multipartite peptide containing at least one secretion modifying region (SMR) peptide from HIV-1 Nef and at least one Clusterin (Clu)-binding peptide (Clu-BP). The subject may have a cancer selected from the group consisting of leukemia, lymphoma, carcinoma, melanoma, sarcoma, germ cell tumor and blastoma.

As used herein, the term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "lymphoma" refers to a group of blood cell tumors that develop from lymphocytes. Exemplary lymphomas include, for example, Hodgkin's lymphomas (HL) and the non-Hodgkin lymphomas.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer. In one embodiment, the subject has breast cancer.

In other embodiments, the present application relates to a method for treating an infectious disease. The method comprises the step of administering to a subject in need thereof an effective amount of a pharmaceutical composition comprising a multipartite peptide containing at least one secretion modifying region (SMR) peptide from HIV-1 Nef and at least one Clusterin (Clu)-binding peptide (Clu-BP).

In some embodiments, the infectious disease is caused by a bacterium. In some embodiments, the infectious disease is caused by a fungus, In some embodiments, the infectious disease is caused by a parasite.

In some embodiments, the infectious disease is caused by a virus selected from the group consisting of human immunodeficiency virus type 1 and type 2 (HIV-1 and HIV-2), human T-cell lymphotrophic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), and combinations thereof. In one embodiment, the subject is infected with HIV-1 or HIV-2.

Dosages and Routes of Administration

Depending on the nature of the disease target, the multipartite peptides of the present disclosure may be administered by any route, including but not limited to any of the various parenteral, gastrointestinal, inhalation, and topical (epicutaneous) routes of administration. Parenteral administration generally involves injections or infusions and includes, for example, intravenous, intraarterial, intratumoral, intracardiac, intramuscular, intravesicular (e.g., to the bladder), intracerebral, intracerebroventricular, intraosseous infusion, intravitreal, intaarticular, intrathecal, epidural, intradermal, subcutaneous, transdermal, and intraperitoneal administration. Gastrointestinal administration includes oral, buccal, sublingual and rectal administration. The route of administration may involve local or systemic delivery of the multipartite peptides.

As a general proposition, the therapeutically effective amount of the multipartite peptide administered will be in the range of about 1 ng/kg body weight/day to about 100 mg/kg body weight/day whether by one or more administrations. In a particular embodiment, the range of multipartite peptide administered is from about 1 ng/kg body weight/day to about 1 μg/kg body weight/day, 1 ng/kg body weight/day to about 100 ng/kg body weight/day, 1 ng/kg body weight/day to about 10 ng/kg body weight/day, 10 ng/kg body weight/day to about 1 μg/kg body weight/day, 10 ng/kg body weight/day to about 100 ng/kg body weight/day, 100 ng/kg body weight/day to about 1 μg/kg body weight/day, 100 ng/kg body weight/day to about 10 μg/kg body weight/day, 1 μg/kg body weight/day to about 10 μg/kg body weight/day, 1 μg/kg body weight/day to about 100 μg/kg body weight/day, 10 μg/kg body weight/day to about 100 μg/kg body weight/day, 10 μg/kg body weight/day to about 1 mg/kg body weight/day, 100 μg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, the multipartite peptide is administered at a dosage range of 1 ng-10 ng per injection, 10 ng-100 ng per injection, 100 ng-1 μg per injection, 1 μg-10 μg per injection, 10 μg-100 μg per injection, 100 μg-1 mg per injection, 1 mg-10 mg per injection, 10 mg-100 mg per injection, and 100 mg-1000 mg per injection. The multipartite peptide may be injected daily, or every 2, 3, 4, 5, 6 and 7 days.

In other embodiments, the dose range of the multipartite peptide administered is from about 1 ng/kg to about 100 mg/kg. In still another particular embodiment, the range of antibody administered is from about 1 ng/kg to about 10 ng/kg, about 10 ng/kg to about 100 ng/kg, about 100 ng/kg to about 1 μg/kg, about 1 μg/kg to about 10 μg/kg, about 10 μg/kg to about 100 μg/kg, about 100 μg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of multipartite peptide administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

The specific dose of multipartite peptide is determined by the particular circumstances of the individual patient including the size, weight, age and sex of the patient, the nature and stage of the disease, the aggressiveness of the disease, and the route of administration of the pharmaceutical composition.

In certain embodiments, the multipartite peptide may be administered at least once per day, typically once, twice, three times or four times per day with the doses given at equal intervals throughout the day and night in order to maintain a constant presence of the drug in order to provide sufficient efficacy. However, a skilled artisan will appreciate that a treatment schedule can be optimized for any given patient, and that administration of compound may occur less frequently than once per day.

Dosage unit form as used herein includes physically discrete units suited as unitary dosages for the subject to be treated; each unit containing a predetermined quantity of the multipartite peptide calculated to produce the desired therapeutic effect in association with the required pharmaceutical carrier. The specification for the dosage unit forms of the invention are dictated by and directly dependent on the unique characteristics of the multipartite peptide and the particular therapeutic effect to be achieved.

Toxicity and therapeutic efficacy of the multipartite peptide of the present disclosure can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Peptides exhibiting large therapeutic indices are preferred. While peptides that exhibit toxic side effects may be used, care should be taken to design a delivery system that targets such peptides to the site of affected tissue in order to minimize potential damage to non-diseased cells and, thereby, reduce side effects.

Data obtained from the cell culture assays and animal studies can be used in formulating a range of dosage for use in humans. The dosage of such peptides lies preferably within a range of circulating concentrations that include the ED50 with little or no toxicity. The dosage may vary within this range depending upon the dosage form employed and the route of administration utilized. For any peptide used in the methods of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

When treating a cancer, any of the multipartite peptides of the present disclosure may be prescribed to be taken in combination with one or more other anti-cancer agents. When used in such combination therapies, the multipartite peptides of the present disclosure and other pharmaceutical agents may be administered simultaneously, by the same or different routes, or at different times during treatment. In particular, the multipartite peptides may be combined with a mortalin siRNA, an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue, and combination thereof.

In some embodiments, the multipartite peptides of the present disclosure is administered in combination or concurrently with a chemotherapeutic agent, such as paclitaxel or cisplatin.

Likewise, when treating an infectious disease, the multipartite peptides of the present disclosure may be prescribed to be taken in combination with one or more antiviral drugs. In certain embodiments, the antiviral drug is a antiretroviral drug selected from the group consisting of: protease inhibitors, nucleoside reverse transcriptase inhibitors, nucleotide reverse transcriptase inhibitors, non-nucleoside reverse transcriptase inhibitors, integrase inhibitors, entry inhibitors, and maturation inhibitors. Exemplary antiviral drugs include, but are not limited to, abacavir, acyclovir, adefovir, amantadine, amdoxovir, amprenavir, antiprotease, apricitabine, arbidol, artemisinin, atazanafir, atripla, azidothymidine (AZT), bevirimat, boceprevir, butylated hydroxytoluene (BHT), cidofovir, combivir, darunavir, delavirdine, didanosine, dipivoxil, docosanol, edoxudine, efavirenz, elvitegravir, elvucitabine, emtricitabine, enfuviritide, entecavir, etravirine, famciclovir, foscarnet, fosamprenavir, ganciclovir, globoidnan A, GSK-572, HIV fusion inhibitors, hypericin, ibalizumab, idoxuridine, immunovir, indinavir, interferons (Types I, II and III), lamivudine, lersivirine, lopinivir, loviride, maraviroc, maribavir, MK-2048, molixan (NOV-205), moroxydine, nelfinavir, nevirapine, nexavir, non-nucleotide HIV RT inhibitors, oseltamivir, pegylated interferons (e.g., peginterferon alfa-2a), penciclovir, pencyclovir, peramivir, pleconaryl, podophyllotoxin, racivir, raltegravir, resquimod, ribavirin, rifampin, rilpivirine, rimantidine, ritonavir, saquinivir, stampidine, stavudine, taribavirin, tenofovir, tipranavir, trifluridine, trizivir, tromantidine, truvada, valaciclovir (Valtrex), valacyclovir, valganciclovir, vicriviroc, vidarabine, vivecon, zalcitabine, zanamivir (Relenza), zidovudine, and combinations thereof.

The treatment may be carried out for a period sufficient to achieve a therapeutic effect. Typically it is contemplated that treatment would be continued indefinitely while the disease state persists, although discontinuation might be indicated if the pharmaceutical compositions no longer produce a beneficial effect. The treating physician will know how to increase, decrease, or interrupt treatment based on patient response.

Production of the Multipartite Peptide

The multipartite peptides of the present disclosure can be chemically synthesized or produced from cells transformed with polynucleotide expression vectors encoding the multipartite peptide. Multipartite peptides of the present disclosure may be synthesized using traditional liquid- or solid-phase synthesis. Fmoc and t-Boc solid phase peptide synthesis (SPPS) can be employed to grow the peptides from carboxy to amino-terminus.

In other embodiments the multipartite peptides are synthesized using recombinant DNA technologies well known to those skilled in the art. Polynucleotide expression vectors can be designed to facilitate preparative expression levels in many different cell hosts, including bacteria, yeast, insect cells, and mammalian cells.

In one aspect, the present disclosure provides a host cell transformed with a polynucleotide or expression vector encoding the multipartite peptide. The host cells can be any bacterial or eukaryotic cell capable of expressing the multipartite peptide-encoding nucleic acids or expression vectors described herein.

In another aspect, a method of producing a multipartite peptide according to the present disclosure comprises culturing a host cell transformed with a multipartite peptide-encoding polynucleotide or expression vector under conditions that allows production of the multipartite peptide, and purifying the multipartite peptide from the cell. The peptides may be produced by culturing a cell transiently or stably expressing a multipartite peptide; and purifying the peptide from the cultured cells. Any cell capable of producing a functional peptide may be used. The peptide-expressing cell may be of prokaryotic or bacterial origin, such as E. coli or it may be of eukaryotic or mammalian origin, such as a human cell. In other embodiments, the cell is a yeast cell or an insect cell. Where the cell is of eukaryotic origin, the peptide-producing cell is preferably stably transformed with a polynucleotide so as to express the peptide.

The present disclosure is further illustrated by the following examples which should not be construed as limiting. The contents of all references, patents and published patent applications cited throughout this application, as well as the Figures and Tables are incorporated herein by reference.

Example 1: Materials and Methods 1-1. Cell Lines, Reagents and Antibodies.

The MCF-7 cell line, a noninvasive estrogen receptor positive (ER+) and MBA-MB-231 cell line (ER negative) were purchased from the American Type Culture Collection (ATCC, Manassas, Va.). MCF-10A cell line, a non-tumorigenic epithelial cell line was also purchased from ATCC. 3-(4,5-dimethylthiazol-2-yl)-2,5-diphenyltetrazolium (MTT), Dulbecco's Modified Eagle's Medium (DMEM) with high glucose and FLUOROBRITE™ phenol red-free DMEM, (MCF-7) were purchased from Thermo Fisher Scientific (Rockford, Ill.) The RPMI 1640 medium (MDA-MB-231 cells) was obtained from Life Technologies Company (Carlsbad, Calif.). The basal medium MEBM and the additive MEGM (MCF-10A cells) were obtained from Lonzal/Clonetics Corporation (Lonza, Walkersville, Md.). Paclitaxel was purchased from Sellck-Chemon, (Houston, Tex.). Cisplatin was purchased from EMD/Millipore (Billerica, Mass.). Annexin V-FITC/PI Apopto and PI Cell Cycle Kits were purchased from Nexcelom Bioscience (Lawrence, Mass.). The CD63 Rabbit polyclonal and Alix goat polyclonal antibodies were purchased from Santa Cruz Biotechnology Inc. (Santa Cruz, Calif.). The PEG-SMRwt-Clu PEG-SMRwt and PEG-SMRmut HIV-1 Nef peptides were purchased from InnoPep Company (San Diego, Calif.).

1-2. Cell Culture.

Cells were cultured in the media described above with addition of exosome-free fetal bovine serum (System Biosciences Inc., Mountain View, Calif.), 100 units/mL penicillin, and 100 mg/mL streptomycin and maintained in a humidified atmosphere at 37° C. and 5% $CO_2$.

1-3. Viability and Proliferation.

Human breast cancer cell lines were seeded into 96-well plates (5000 cells/well) and treated for 24 hours with various concentrations of SMR peptides including PEG-SMRwt-Clu, PEG-SMRwt and PEG-SMRmut to determine IC50 (inhibition concentration). Cell proliferation was determined using the MTT assay (Molecular Devices, Sunnyvale, Calif.). Control experiments were performed with MTT treated cells alone and untreated cells, and on this basis, the incubation times of 24 hr and 48 hr were used for an MTT assay of peptide-treated cells (Stockerta J C. et al., 2012 and Riss T L. et al., 2015).

1-4. Cell Cycle Analysis.

MCF-7 and MDA-MB-231 breast cancer cells were cultured into 6-well plates at $4 \times 10^5$ cells per well and treated with either paclitaxel and cisplatin or combined with PEG-SMRwt-CLU peptide for 24 and 48 hours. Cell cycle analysis was performed using a propidium iodide cell cycle assay and measured using a Cellometer (Nexcelom, MA). Further experiments were performed with SMR at IC50 concentration; the results showed 1.12 µM of PEG-SMRwt-Clu, 0.28 µM of PEG-SMRwt on MCF-7 cells for 24 hours and 0.28 µM of PEG-SMRwt-Clu, 0.42 µM of PEG-SMRwt on MDA-MB-231 cells for 24 hours for each cell time two stage. Breast cancer cells were seeded into 96-well plates at $5 \times 10^3$ cells/ml, and treated with either 1.6 µM//mL of paclitaxel, or 3 mg/mL cisplatin, 1.12 µM/mL PEG-SMRwt-CLU peptide, SMR peptide combined with paclitaxel or with cisplatin (MCF-7 cells). Alternatively 1.6 µM/mL paclitaxel or 2 mg/mL cisplatin or 0.28 µM/mL of PEG-SMR-CLU peptide, or the peptide combined with each of these drugs was used forMDA-MB-231 cells. The concentrations for cisplatin and paclitaxel were experimentally determined IC50 dosages for the different cell types (data not shown). At the end of the 24 hr or 48 hr incubations, the cells were assessed by the Cellometry imaging cytometry assay.

All above steps were done on MCF-7 and MDA-MB-231 cells separately. In order to further understand whether this peptide functions synergistically with chemotherapeutic drugs, 6 groups of cancer cells were treated as follows: 1) untreated, 2) PEG-SMRwt-CLU, 3) paclitaxel, 4) paclitaxel in combination with PEG-SMRwt-CLU, 5) cisplatin, 6) cisplatin in combination with PEG-SMRwt-CLU.

1-5. Assessment of Apoptosis.

Breast cancer cells were seeded into 6-well plates at $4 \times 10^5$ cells per well and treated with either paclitaxel or cisplatin or various concentrations of SMR peptides for 24 hours or different time point. SMR as described above. Apoptosis was determined the using AnnexinV-FITC detection kit (Nexcelom, MA) and visualized by Cellometer imaging cytometry.

1-6. Exosome Isolation and Purification.

Exosomes were isolated from breast cancer cells by differential centrifugation as previously described (Ali S A. et al., 2010). Untreated tumor cells were used as a control. Briefly, the above treated and untreated cell supernatants were centrifuged at 400×g for 10 minutes. The supernatants were transferred to a clear tube and centrifuged at 10,000×g for 30 minutes. The supernatants from the second spin were ultracentrifuged at 200,000×g for 2 hours to pellet exosomes. Finally, the exosome pellets were re-suspended with PBS and stored at 4° C. until used for analysis.

1-7. Exosome Characterization by Acetylcholinesterase (AchE) Assay.

Purified exosomes were quantitated by measurement of AchE as described (Ellman et al., 1961). Briefly, a 100 mM dithibionitrobenzoic (DTNB) solution was prepared for use as a stock color indicator, and a 28.9 mg/mL acetylthiocholine iodide in PBS solution was prepared as a stock substrate. The stock substrate stock can be stored at −20° C. up to one month, while the color indicator can be stored at 4° C. for two weeks. A working solution was prepared by mixing 10 mL of PBS with 200 µL of Substrate and 500 µl of DTNB. 50 µL of each exosome sample was transferred to 96 well microtitre plates, and a standard curve was prepared using AchE from 0.98 mU/mL to 2000 mU/mL. After 50 µL of standards were added into separate wells, 200 μL of the working solution was added to all wells. After 20 min incubation, AchE activity was measured at 450 nm using a SpectroMax M5 fluorimeter.

1-8. Exosome Nanoparticle Tracking Analysis (NTA).

Analysis of absolute size distribution of exosomes was performed using NanoSight LM10 with NTA2.3 (NanoSight Ltd., Minton Park, UK). Particles were automatically tracked and sized based on Brownian motion and the diffusion coefficient. After isolation, the untreated and treated breast cancer exosomes were re-suspended in 0.5 mL of PBS. Control medium and filtered PBS were used as controls in this technique. The NTA measurement conditions were: temperature=21.0+/−0.5° C.; viscosity=0.99+/−0.01 cP, frames per second=25, measurement time=30 s. The detection threshold was similar in all samples. Two recordings were performed for each sample.

1-9. Western Blot Analysis.

Exosomes were isolated from culture supernatants as described above. Protein concentration was determined by measuring absorbance at 280 nm (Nanodrop 2000). Protein samples were denatured in SDS-PAGE sample buffer by heating at 95° C. for 15 min. Criterion TGX Precast Gels (4-20% Bio-Rad, Richmond, Calif.) were used to separate the proteins and blotted as previously described (Huang M B. et al 2004). Blots were incubated with the primary antibodies, anti-CD63 and anti-Alix, followed by goat or rabbit anti-Ig secondary antibodies. Specific bands were detected using ECL chemiluminescent substrate (Santa Cruz Biotechnology, Santa Cruz, Calif.) and visualized on the ImageQuant LAS 4000 imaging system (GE Healthcare, Piscataway, N.J. 08854).

1-10. Fluorescent N-Rh-PE Measurement.

The fluorescent phospholipid analog N-Rh-PE [N-(lissamine rhodamine B sulfonyl) phosphatidyl ethanolamine] is a lipid marker of exosomes and intraluminal vesicles of multivesicular bodies as previously described (Willem J et al., 1990). Briefly, 10 mM of the N-Rh-PE was stored in chloroform/methanol (2:1). A 5 μM N-Rh-PE solution in a pre-cooled reaction medium was then added to the treated with MCF-7 breast cancer cells transfected with siRNA-Negative or siRNA-HSPA9, and then were incubated at 4° C. for 1 h. After this incubation period, the medium was removed and the cells were extensively washed with cold medium to remove excess unbound lipids. Labeled cells were cultured in complete RPMI-1640 with 10% exosome-depleted FBS medium heat inactivated at 37° C. overnight. Measurement of N-Rh-PE in the collected supernatants/exosomes was carried out using a spectrometer at 550 nm and 590 nm excitation and emission wavelengths, respectively.

1-11. Transfection with Mortalin Antibody.

MCF-7 breast cancer cells were transfected with mortalin antibody using a Chariot kit (Active Motif, Carlsbad, Calif.) in accordance with the manufacturer's protocol. Following a 48 hour incubation of these cells, the exosomes were isolated and measured via AchE assay and NanoSight analysis.

1-12. Transient Transfection with Small Interfering RNA (siRNA).

MCF-7 breast cancer cells were transfected with double-stranded siRNAs using Amaxa's Nucleofector kit (Lonza Walkersville Inc., Walkersville, Md.) in accordance with the manufacturer's protocol. Transfection of plasmids was carried out using Amaxa Biosystems Nucleofector II as recommended by the supplier. Mortalin siRNAs were prepared as previously described (Shelton M N et al., 2012). Following transfection, the cells were incubated at 37° C. for 24, 48, 72 and 96 hours, and exosomes were isolated and measured by AchE assay and Western blotting.

1-13. Statistical Analysis.

Data was expressed as the mean±standard deviation (S.D.). A two-sample t-Test assuming equal variances was used to compare the differences between controls and treated samples in each group. A value of p≤0.05 was considered to be statistically significant.

Example 2: SMR Peptides Inhibit Cell Growth of Breast Cancer Cells

Breast cancer cells were treated for 24 hours with increasing concentrations (35 nM/mL, 70 nM/mL, 140 nM/mL, 280 nM/mL, 560 nM/mL and 1120 nM/mL) of PEG-SMRwt-Clu peptide in combination with either PEG-SMRwt or PEG-SMRmut peptides as controls. Both peptides containing the SMRwt sequence inhibited breast cancer cell growth in a dose-dependent manner (FIG. 1). For MCF-7 cells, 50% inhibition was seen with 1.12 μM/mL of PEG-SMRwt-Clu and 0.28 μM/mL of PEG-SMRwt. For MDA-MB-231 cells 50% inhibition was achieved with 0.28 μM/mL of PEG-SMRwt-Clu and 0.42 μM/mL of PEG-SMRwt. The PEG-SMRmut peptide did not inhibit proliferation.

Example 3: SMRwt Peptides Induce Cell Cycle Arrest in Breast Cancer Cells

Figure 2:
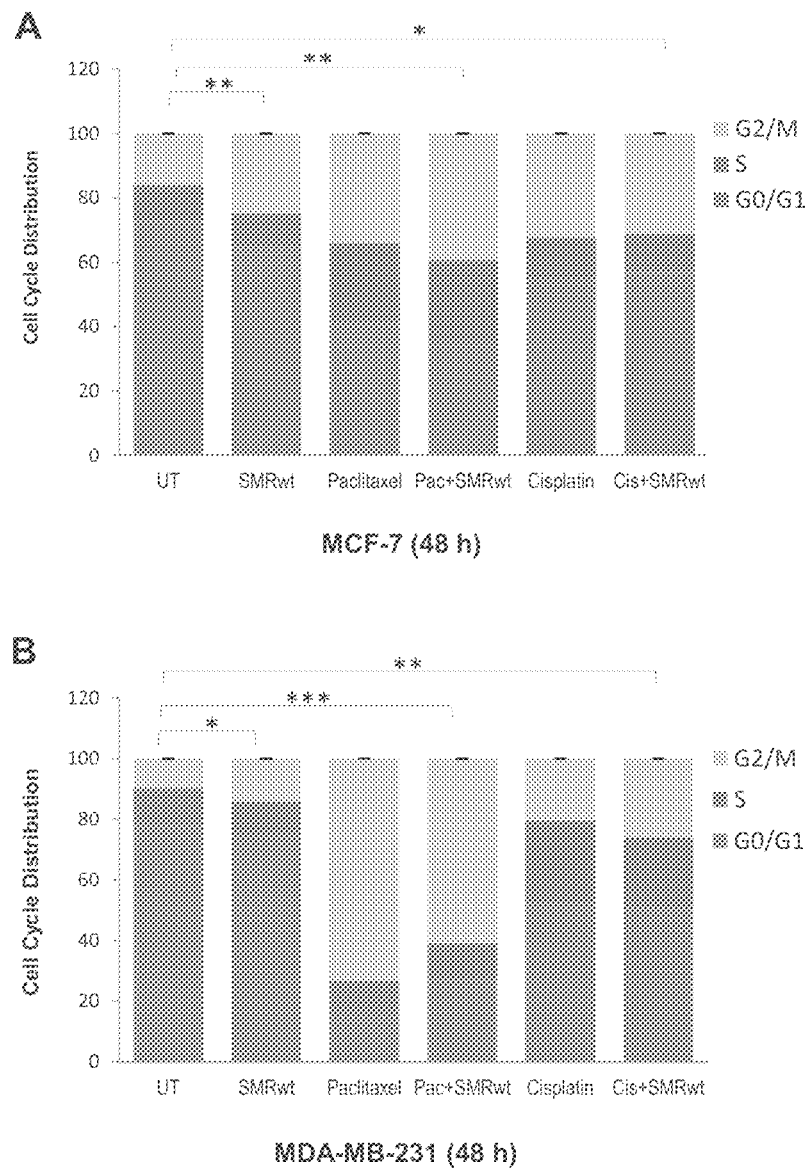
FIG. 2 shows that PEG-SMRwt-CLU peptide antagonist and chemotherapeutics induced cell cycle arrest in MCF-7 and MDA-MB-231 breast cancer cells. Cells were treated 48 hr with SMR peptides, alone or in combination with paclitaxel or cisplatin, and were assayed by Cellometer imaging cytometry, indicating percentage of MCF-7 (Panel A) and MDA-MB-231 (Panel B) in various cell cycle phases. Results of two independent experiments are shown. Significant differences relative to untreated control are indicated as follows: $*p<0.01$, $**p<0.001$ for MCF-7 cells, and $*p<0.02$, $p<0.01$, $*p<0.0001$ for MDA-MB-231 cells.

The data indicated that PEG-SMRwt-CLU peptides induced cell cycle arrest in MCF-7 cells and MDA-MB-231 cells assayed at 48 hours (FIG. 2). When cells were treated with the PEG-SMRwt-CLU peptide, or the peptide combined with paclitaxel or cisplatin, they were blocked in G2/M phase, indicating that PEG-SMRwt-Clu peptides contribute to induction of G2/M arrest in breast cancer cells.

Figure 3:
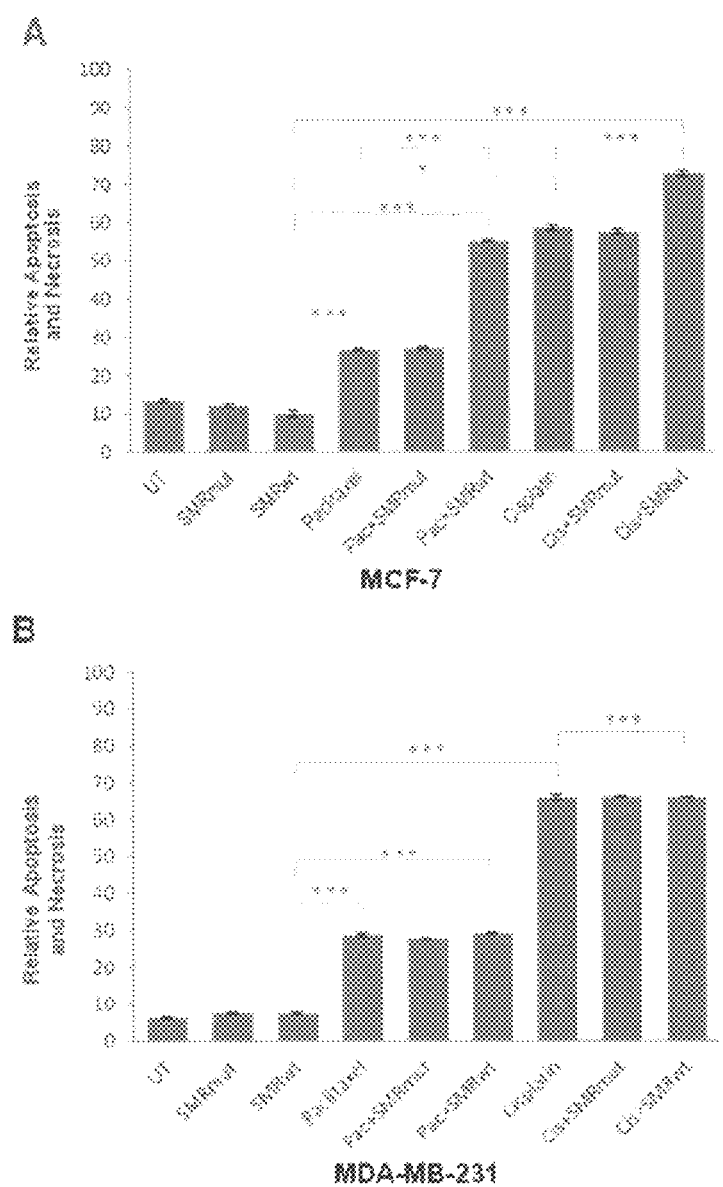
FIG. 3 shows that PEG-SMRwt-CLU peptide antagonist increased cytotoxicity in MCF-7 but not in MDA-MB-231 breast cancer cells. Percentage of apoptotic cells (Panel A) MCF-7 and (Panel B) MDA-MB-231, as determined by Annexin V-FITC assay of cells treated for 48 hr with peptide alone or combined with paclitaxel or cisplatin. Error bars represent mean±SD of four independent experiments. Significant differences relative to SMRwt peptide are indicated as follows: $*p<0.01$, $***p<0.0001$.

Example 4: SMRwt Peptides Increased the Sensitivity of Breast Cancer Cells to Cisplatin and Paclitaxel in MCF-7 Breast Cancer Cells In a separate experiment, MCF-7 and MDA-MB-231 cells were treated with either PEG-SMRwt-CLU or PEG-SMRmut-CLU alone, or in further combination with paclitaxel or cisplatin and then assayed for apoptosis by Annexin V-FITC/PI assay. Both of these cell lines showed increased apoptosis relative to the unmodified control peptides after the incubation with paclitaxel and cisplatin for 48 hours (FIG. 3). Interestingly, the PEG-SMRwt-Clu peptide increased the level of drug-induced apoptosis in MCF-7 cells, but not in MDA-MB-231 cells.

Example 5: SMR Peptides Block Exosome Release in Breast Cancer Cells

Acetylcholinesterase (AchE) assays, NanoSight analysis and Western blot analysis were performed to characterize exosomes released from MCF-7 and MDA-MB-231 human breast cancer cells treated for 48 hr with the various peptides. The results indicated that exosome release was inhibited by the SMRwt peptides.

AchE activity in exosomes was assayed and the results of this analysis is shown in FIGS. 4A and 4B. In MCF-7 cells, the control exosomes were found to contain 113.49 mU/mL of AchE activity. In contrast, 41.95 mU/mL of activity was found in cells treated with PEG-SMRwt-CLU peptide; 51.87 mU/mL activity was found in cells treated with PEG- SMRwt-CLU in combination with paclitaxel; and 16.95 mU/mL activity was found in cells treated with PEG-SMRwt-CLU in combination with (FIG. 4A). In MDA-MB-231 cells, the control exosomes contained 118.48 mU/mL of AchE activity, whereas 66.77 mU/mL activity was found in cells treated with PEG-SMRwt-CLU peptide; 64.15 mU/mL activity was found in cells treated with PEG-SMRwt-CLU peptide in combination with paclitaxel; and 27.0 mU/mL activity was found in cells treated with PEG-SMRwt-CLU in combination with cisplatin (FIG. 4B).

Figure 4:
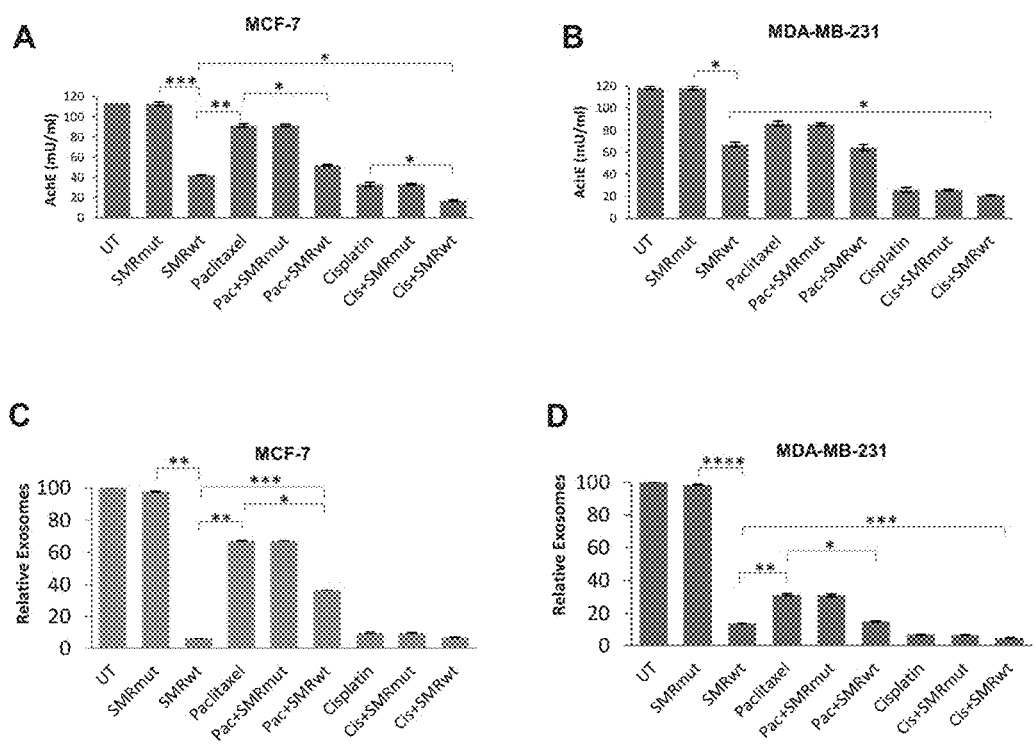
FIG. 4 shows that PEG-SMRwt-CLU peptide antagonist blocks exosome release from MCF-7 and MDA-MB-231 cells. Cells were treated for 48 hr with peptide alone or combined with paclitaxel or cisplatin. Panels A and B show relative level of exosomes released from MCF-7 and MDA-MB-231 cells respectively, determined by AchE assay. Error bars represent mean±SD of four independent experiments. Significant differences relative to SMRwt peptide: $*p<0.01$, $p<0.001$, $*p<0.0001$ for MCF-7 cells; and $*p<0.01$ for MDA-MB-231 cells. Panels C and D show relative numbers of exosomes released by MCF-7 and MDA-MB-231 cells respectively, as determined by Nanosight measurement. Error bars represent mean±SD of two independent experiments. Significant differences relative to SMRwt peptide: $*p<0.01$, $p<0.001$, $*p<0.0001$ for MCF-7 cells and $*p<0.03$, $p<0.02$, $*p<0.01$ and $****p<0.001$ on MDA-MB-231 cells.

Analysis of exosomes concentration and size distribution was assayed by NanoSight LM10 Nanoparticle Tracking Analysis (NTA). With NTA, particles are automatically tracked and sized based on Brownian motion and the associated diffusion coefficient. Before analysis of the samples by NTA, it was determined that salt aggregates from the PBS did not contribute to background and the equipment was free of contaminant particles. The untreated MCF-7 cell control medium showed a considerable number of particles ($5.16 \times 10^9$ particles/ml) (FIG. 4 Panel C). However, a reduced number of particles was found in MCF-7 cells treated with PEG-SMRwt-CLU ($3.28 \times 10^8$ particles/ml, $p<2.40E-06$), PEG-SMRwt-CLU in combination with paclitaxel ($5.7 \times 10^8$ particles/mL, $p<0.0008$) and PEG-SMRwt-CLU in combination with cisplatin ($3.77 \times 10^8$ particles/mL, $p<0.0001$) (FIG. 4 Panel C).

Similarly, whereas control media from MDA-MB-231 cultures also showed a considerable number of particles ($4.7 \times 10^9$ particles/ml), a reduced number of particles was found in MDA-MB-231 cells treated with PEG-SMRwt-CLU peptide ($6.8 \times 10^8$ particles/ml, $p<3.96E-05$), PEG-SMRwt-CLU peptide in combination with paclitaxel ($7.5 \times 10^8$ particles/mL, $p<0.001$) and PEG-SMRwt-CLU peptide in combination with cisplatin ($3.06 \times 10^8$ particles/mL, $p<5.37E-05$) (FIG. 4 Panel D). By NTA analysis, the size of the exosomes was estimated to range between 30 to 47 nm in both breast cancer cell lines.

Figure 5:
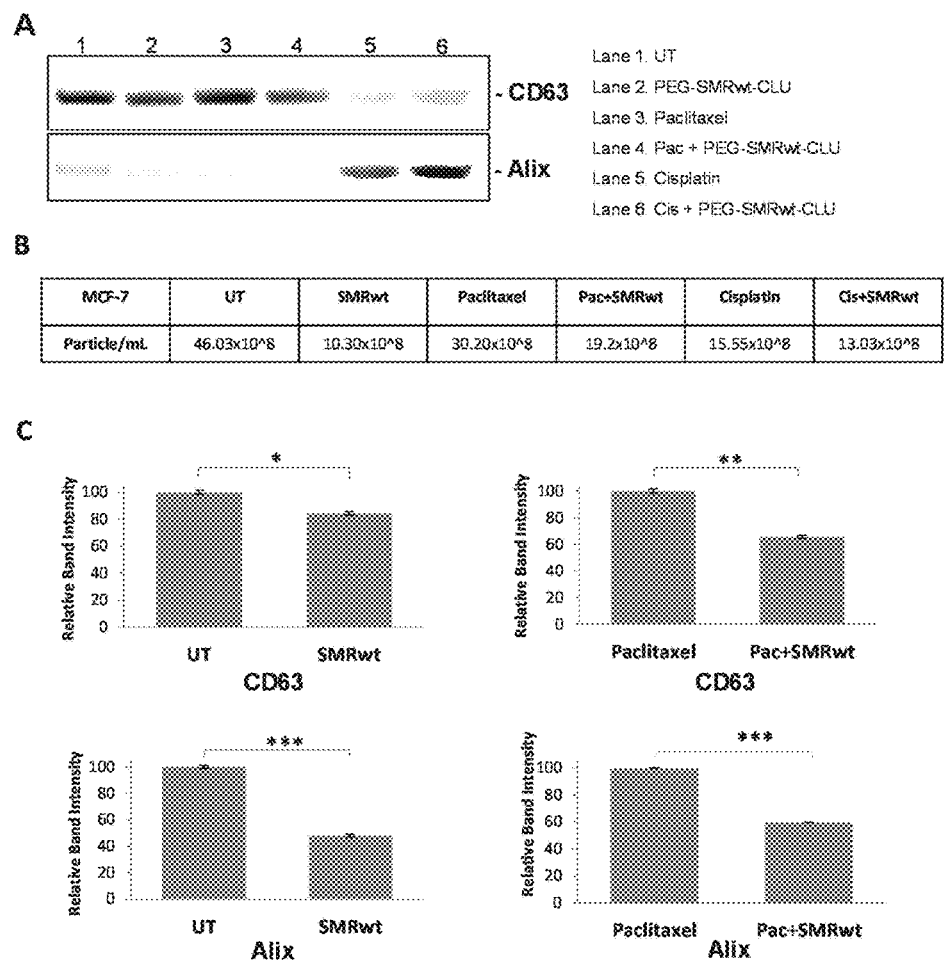
FIG. 5 shows that exosome-specific proteins can be detected on exosomes from MCF-7 breast cancer cells. Cells were treated for 48 hr with SMRwt peptide alone or combined with paclitaxel or cisplatin. Panel A: Expression of exosome proteins by Western blot analysis. Panel B: Exosome numbers were measured by NanoSight. Panel C: Densitometry analysis showing relative intensity of bands. Data represent the mean±SD of three independent experiments. Significant differences relative to treatment with peptide are indicated as follows: $*p<0.01$, $p<0.001$, $*p<0.0001$.
Figure 6:
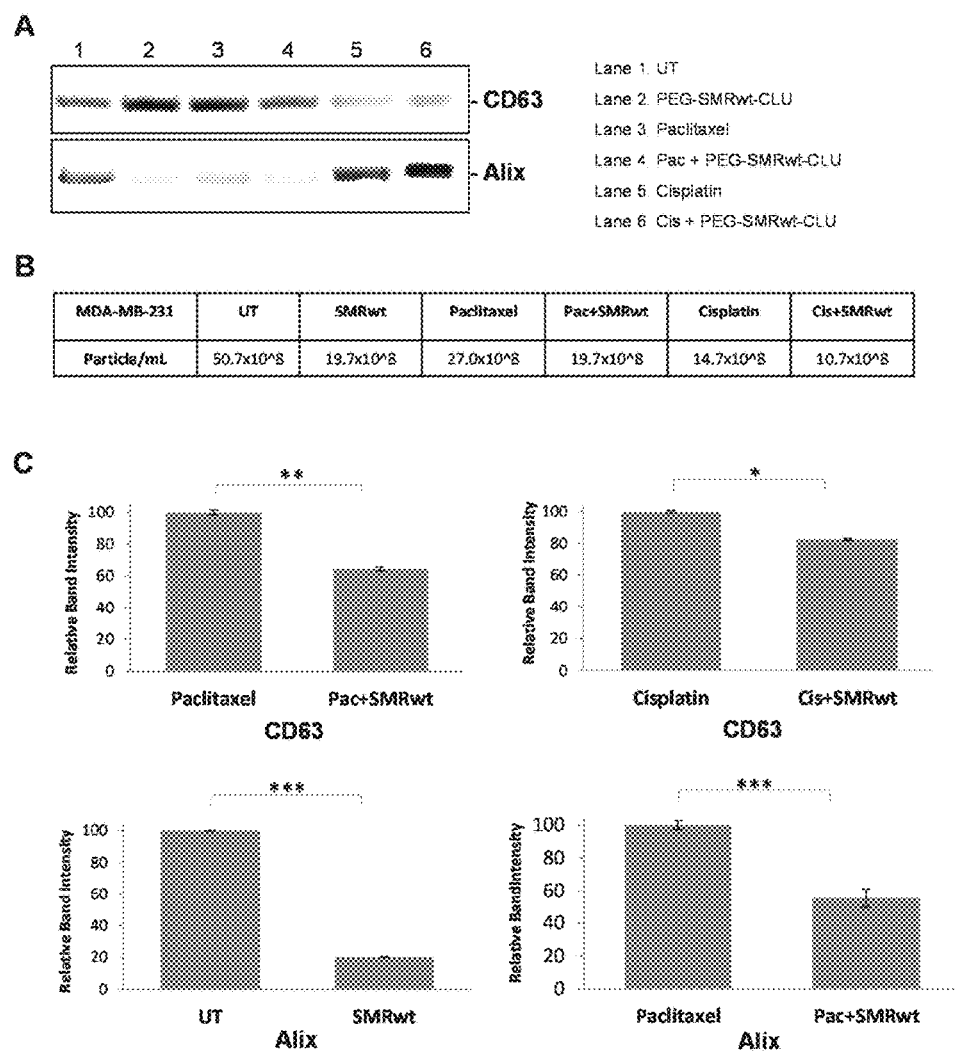
FIG. 6 shows that exosome-specific proteins can be detected on exosomes from MDA-MB-231 breast cancer cells. Cells were treated for 48 hr with SMRwt peptide alone or combined with paclitaxel or cisplatin. Panel A shows Expression of exosome proteins by Western blot analysis. Exosome numbers were measured by NanoSight (Panel B) and densitometry analysis shows relative intensity of bands (Panel C). Data represent the mean±SD of three independent experiments. Significant differences relative to treatment with peptide are indicated as follows: $*p<0.01$, $p<0.001$, $**p<0.0001$.

Finally, Western blot analysis was used to detect exosome proteins in control- and peptide-treated cultures. The results of this analysis revealed the presence of human CD63 and Alix markers in the all exosomes isolated from MCF-7 cells (FIG. 5) and MDA-MB-231 cells (FIG. 6). Control exosomes showed higher expression of human CD63 from MCF-7 cells and higher expression of Alix from MDA-MB-231 cells.

Figure 7:
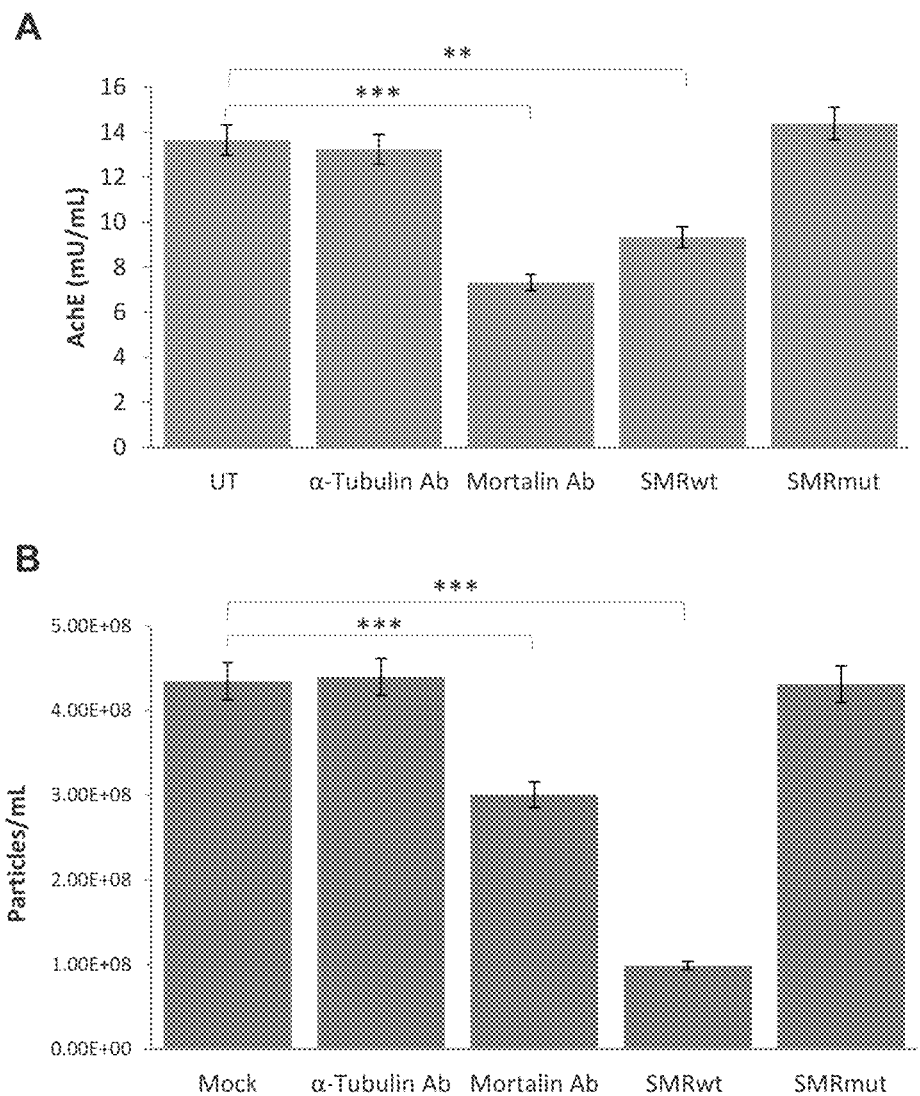
FIG. 7 shows that antibody to mortalin inhibits exosome secretion from MCF-7 breast cancer cells. MCF-7 cells were either transfected with antibodies to mortalin or alpha-tubulin, or treated with SMRwt or SMRmut peptides. Panel A: Relative exosome release level after 48 hr by AchE assay. Panel B: Relative numbers of exosomes released after 48 hr by NanoSight analysis. Error bars represent the mean±SD of three independent experiments. Significant differences relative to untreated cells: $*p<0.0001$, $**p<0.0001$.

Example 6: Blocking the SMR-Mortalin Interaction Blocks Exosome Release in Breast Cancer Cells A previous study identified the HSP70 family protein, mortalin (encoded by HSPA9) as a binding partner for HIV-1 Nef SMR, and showed that disruption of HIV-1 Nef SMR-mortalin binding interfered with exosome release (Shelton M N. et al., 2012). To test whether an analogous interaction accounts for the observed PEG-SMRwt-CLU effect on exosome release from breast cancer cells, MCF-7 cells were transfected with antibody to mortalin or antibody to α-tubulin as a control. The anti-mortalin treated cells were found to be significantly impaired in exosome release as measured by AchE assay (FIG. 7 Panel A) and slightly less so when measured by NTA assay (FIG. 7 Panel B). The effect of treatment with anti-mortalin was similar to the effect of treating MCF-7 cells with PEG-SMRwt-CLU peptide.

Figure 8:
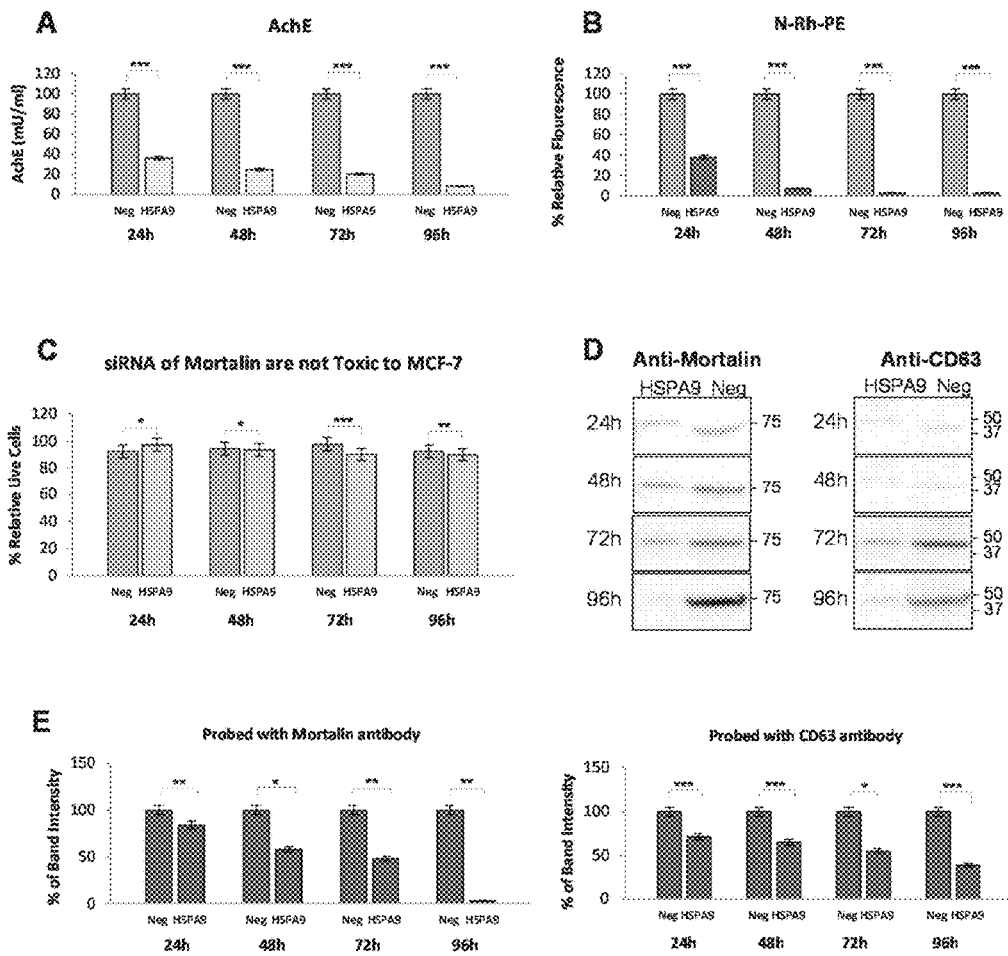
FIG. 8 shows exosome secretion is decreased in MCF-7 breast cancer cells by knockdown of mortalin expression. MCF-7 cells were transfected with clones expressing siRNA against either mortalin (HSPA9) or a negative control RNA. Exosomes were isolated and analyzed after 24, 48, 72, and 96 hr for changes in level of exosome secretion by AchE assay (Panel A). Significant differences relative to controls are indicated: $*p<0.0001$, and exosome secretion by N-Rh-PE (Panel B). Significant differences relative to controls are indicated: $*p<0.0001$. Panel C: percentage of live cells remaining at each time point, $*p<0.05$, $p<0.002$, $*p<0.0001$. Panel D: mortalin and CD63 protein expression levels by Western blotting. Panel E: Densitometry analysis of Western blot data. Significant differences relative to controls are indicated: $*p<0.01$, $p<0.001$, $*p<0.0001$.

To further validate the significance of this mortalin-mediated process in cancer cells, expression of mortalin protein was knocked down by transfecting MCF-7 cells with a plasmid construct expressing a mortalin siRNA. The mortalin siRNAs were found to block exosome secretion as evidenced by AchE assay and membrane fluorescence (N-Rh-PE) assays at all time points tested (FIGS. 8 Panel A and 8 Panel B) in the absence of any cell toxicity (FIG. 8 Panel C). The exosomes from siRNA-transfected cells were further assayed for expression of mortalin and the exosome marker CD63, a tetraspanins by Western blot analysis. The results of this analysis showed that expression of both mortalin and CD63 was significantly decreased at 48 h on through to 96 h (FIGS. 8 Panel D and 8 Panel E).

The above description is for the purpose of teaching the person of ordinary skill in the art how to practice the present disclosure, and it is not intended to detail all those obvious modifications and variations of it which will become apparent to the skilled worker upon reading the description. It is intended, however, that all such obvious modifications and variations be included within the scope of the present embodiment, which is defined by the following claims. The claims are intended to cover the claimed components and steps in any sequence that is effective to meet the objectives there intended, unless the context specifically indicates the contrary.

What is claimed is:

1. A multipartite peptide that inhibits release of exosomes in a cell,
wherein the peptide comprises an amino acid sequence selected from the group consisting of VGFPVAAVGFPVHPLSKHPYWSQP (SEQ ID NO:6), VGFPVAAVGFPVAAHPLSKHPYWSQP (SEQ ID NO:7), and VGFPVAAVGFPVAAHPLSKHPYWSQPAAHPLSKHPYWSQP (SEQ ID NO:8).

2. A polynucleotide encoding the multipartite peptide of claim 1.

3. An expression vector comprising the polynucleotide of claim 2 operably linked to a regulatory sequence.

4. A cell comprising the expression vector of claim 3.

5. A pharmaceutical composition comprising the multipartite peptide of claim 1 and a pharmaceutically acceptable carrier.

6. The pharmaceutical composition of claim 5, wherein the multipartite peptide is pegylated.

7. The pharmaceutical composition of claim 5, wherein the multipartite peptide is further linked to an endopeptidase cleavage signal.

8. A method for treating a cancer, comprising:
administering to a subject in need of such treatment an effective amount of the pharmaceutical composition of claim 5.

9. The method of claim 8, wherein the subject has breast cancer.

10. The method of claim 8, further comprising the step of administering to the subject a chemotherapeutic agent.

11. The method of claim 10, wherein the chemotherapeutic agent is paclitaxel or cisplatin.

12. A method for treating an infectious disease, comprising:
administering to a subject in need of such treatment an effective amount of the pharmaceutical composition of claim 5.

13. The method of claim 12, wherein the subject is infected with HIV-1 or HIV-2.

* * * * *